(12) United States Patent
Khasanov et al.

(10) Patent No.: US 6,525,200 B1
(45) Date of Patent: Feb. 25, 2003

(54) MULTICYCLIC AROMATIC COMPOUNDS AND USES THEREOF

(75) Inventors: Alisher B. Khasanov, Carlsbad, CA (US); Thomas W. Bell, Reno, NV (US)

(73) Assignee: Roche Diagnostics Corporation, Indianapolis, IN (US)

( * ) Notice: Subject to any disclaimer, the term of this patent is extended or adjusted under 35 U.S.C. 154(b) by 298 days.

(21) Appl. No.: 09/636,275

(22) Filed: Aug. 10, 2000

(51) Int. Cl.$^7$ ............... C07D 471/22; C07D 401/14; G01H 33/53
(52) U.S. Cl. ............... 546/28; 544/310; 544/323; 546/41; 546/36; 252/301.25; 252/700
(58) Field of Search ............... 546/28, 36, 41; 544/310, 333; 252/301.26, 700

(56) References Cited

U.S. PATENT DOCUMENTS

| | | | |
|---|---|---|---|
| 5,030,728 A | 7/1991 | Bell | 546/27 |
| 5,283,333 A | 2/1994 | Bell | 546/27 |
| 5,464,587 A | 11/1995 | Lippitsch et al. | |

OTHER PUBLICATIONS

Barton et al., "The Invention of New Radical Chain Reactions–, Part VIII", *Tetrahedron* 1985, 41, 3901–3924.
Bell et al. "Torand Synthesis by Trimerization—New Receptors for Guandinium", (*Angew. Chem. Int. Ed. Eng.* 1990, 29, 923–925).
Bell et al., "Hexagonal Lattice Hosts for Urea. A New Series of Designed Heterocyclic Receptors", *J. Am. Chem. Soc.* 1988, 110, 3673.
Bell et al., "Binding biomolecules with designed, hydrogen-bonding receptors", *Pure & Appl. Chem.* 1998, 70, 2371–2377.
Bell et al., "A Hydrogen–Bonding Receptor That Binds Urea with High Affinity", *Angew. Chem. Int. Ed. Engl.* 1997, 36, 1536–1538).
Bell et al., "A Small–Molecule Guanidinium Receptor: The Arginine Cork", *Angew. Chem., Int. Ed. Engl.*, 1999, 38, 2543–2547.
Bell et al., "Hexagonal Lattice Appraoch to Molecular Receptors", *Inclusion Phenomena and Molecular Recognition*, Atwood, J. L., Ed. (Plenum, New York, 1990) pp. 49–56.
Davoll et al., "Synthesis of Divine (2: 4–Diamino–3 5 : 6–dihdroxypyrimidine) and Other Derivatives of 4 : 5(5:6)—Dihydroxypyrimidine", *J. Chem. Soc.* 1956, 2124–2131.

Eliseev et al., "Use of Molecular Recognition To Drive Chemical Evolution", *J. Am. Chem. Soc.* 1997, 119, 1147–1148.
Foley et al., "Neutral Conversion af Aldoximes into Nitriles at Low Temperature", *J. Chem. Soc., Chem. Commun.* 1973, 628–629.
Johnson et al., "Polyfunctional Aliphatic Compounds.", *J. Org. Chem.* 1962, 27, 2473–2478.
Jansen et al., "Liquid Chromatographic Determination of Guanidines with an Anion Exchange Column Used Simultaneously as Separator and Postcolumn Reagent Generator", *Anal. Chem.*, 58, 1380–1383 (1986).
Lehn et al., "Stable and Selective Guanidinium and Imidazolium Complexes of a Macrocyclic Receptor Molecule", *J. Chem. Soc., Chem. Commun.* 1979, 296–298).
Majewicz et al., "A Facile Synthesis of 2–Aminonicotinaldehyde", *J. Org. Chem.* 1974, 39, 720.
Pinner, "Ueber Derivate des Oximidoäthers und des Succinimidoäthers", *Ber.* 1883, 16, 1654.
Pinner, "Einwirkung von Essigsäureanhydrid auf die Amidine", *Ber.* 1884, 17, 170.
Schrader, "Strong Binding of Alkylguandidium Ions by Molecular Tweezers: An Artifical Selective Arginine Receptor Molecule with a Biomimetic Recognition Pattern", *Chem. Eur. J.* 1997, 3, 1537–1541.
Wright, "Maintenance Hemodialysis", G. K. Hall: Boston 1981, Chpt. 1.
Zimmerman et al., "Synthesis and Structure of Molecular Tweezers Containing Active Site Functionality", *J. Am. Chem. Soc.* 1991, 113, 183–196.

*Primary Examiner*—Charanjit S. Aulakh
(74) *Attorney, Agent, or Firm*—Pitney, Hardin, Kipp & Szuch LLP

(57) ABSTRACT

Multicyclic aromatic compounds useful as complexing agents having the general formula:

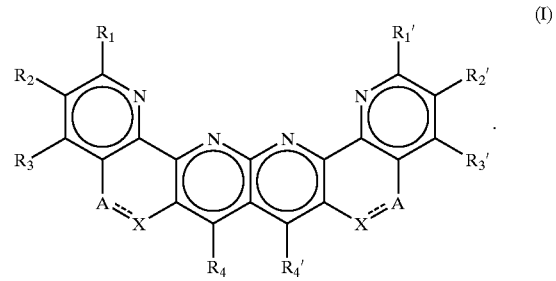

(I)

Methods of complexing and quantitating a component in a sample such as urea or guanidine are also disclosed.

21 Claims, 12 Drawing Sheets

Reaction Scheme for Synthesis of Compound IA (5).

Reaction Scheme for Compound IB (6)

Reaction scheme for Compound IC (8).

Reaction scheme for Compound ID (9).

Reaction Scheme for Compound IE (11).

MULTICYCLIC AROMATIC COMPOUNDS AND USES THEREOF

The present invention relates to multicyclic aromatic compounds, and more particularly to multicyclic aromatic compounds useful as complexing agents.

BACKGROUND OF THE INVENTION

Small biological molecules such as urea, guanidine, their derivatives and their acid addition salts are present in human bodily fluids, such as serum and urine, where they can serve as indications of various disorders. For example, the concentration of urea in blood serum is used as an indication of renal dysfunction, such as uremia, and defects in nitrogen metabolism; see for example, (Wright, "Maintenance Hemodialysis", G. K. Hall: Boston (1981), Chpt. 1).

Assays for determining the concentration of guanidine and its derivatives in blood serum, urine and hemodialysate are useful in detecting certain metabolic disorders such as hyperargininemia and argininosuccinic acidurea; (Kobayashi, et al., Anal. Chem., 58, 1380–1383 (1986)).

Small molecules designed to bind urea, guanidine and their derivatives and signal this event can be applied for determination of analyte concentration in bodily fluids. Previously, a hexagonal lattice approach for urea receptors was developed by Bell's research group (Bell et al., in *Inclusion Phenomena and Molecular Recognition*, Atwood, J. L., Ed. (Plenum, New York, 1990) pp. 49–56). For example, fused pyridine rings in 1 and 2 form a rigid backbone for hydrogen bond donor/acceptor atoms (FIG. 1). The complexes of 1 and 2 with urea are stabilized by four and six hydrogen bonds, respectively. The dissociation constants ($K_d$) of these complexes were measured in organic solvents with low polarity. Thus, the $K_d$ for complex 1 in water-saturated chloroform was calculated as 0.33 mM and for complex 2 in 1:1 $CDCl_3$/DMSO mixture as 0.07 mM (Bell et al. *J. Am. Chem. Soc.* 1988, 110, 3673; Bell et al., in *Inclusion Phenomena and Molecular Recognition*, Atwood, J. L., Ed. (Plenum, New York, 1990) pp. 49–56; Bell et al. *Pure & Appl. Chem.* 1998, 70, 2371–2377; Bell et al., *Angew. Chem. Int. Ed. Engl.* 1997, 36, 1536–1538). Although the stability of complexes 1 and 2 in relatively non-polar solvents is significant, it is well known that corresponding complexes stability in aqueous solutions is generally weaker by several orders of magnitude. Lack of solubility of 1 and 2 in aqueous medium, due to lipophilicity of these molecules, precludes the use of these receptors in water-based solutions, such as serum and urine.

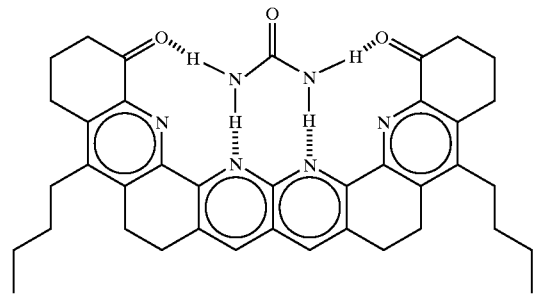

1·Urea

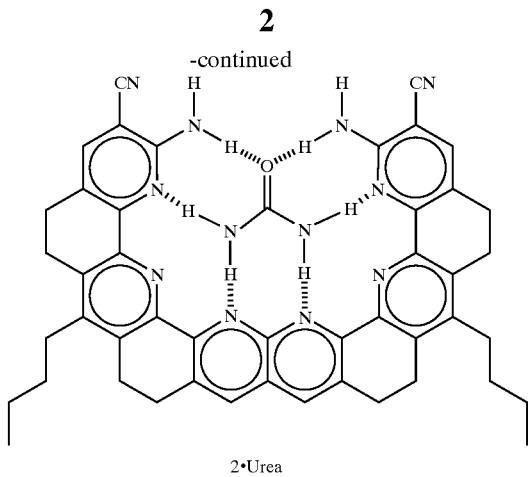

2·Urea

Since the 1970's almost all designed receptors for guanidinium have been crown ether derivatives which lack chromogenic or fluorescence signaling (e.g., Lehn et al., *J. Chem. Soc., Chem. Commun.* 1979, 296–298). In 1990 Bell et al. (*Angew. Chem. Int. Ed. Eng.* 1990, 29, 923–925) reported an alternative to flexible crown ethers—also cyclic, but rigid and preorganized, a torand which forms a highly stable complex with unsubstituted guanidinium ion in methanol/dichloromethane mixture. However, the reported torand lacks signaling mechanism and is not soluble in water. Another type of partially flexible receptors for guanidinium ion, called molecular "tweezer", which incorporate two carboxylate groups (Eliseev et al., *J. Am. Chem. Soc.* 1997, 119, 1147–1148) and two phosphonate groups (Schrader, *Chem. Eur. J.* 1997, 3, 1537–1541), only weakly bind guanidinium ions in methanol.

Recently reported water-soluble receptor for guanidinium ion, the "arginine cork" (3) strongly binds alkylguanidinium ions in water (Bell et al., *Angew. Chem., Int. Ed. Engl.*, 1999, 38, 2543–2547). The dissociation constant of the complex of 3 with methylguanidinium ion in water was found as 4.3 mM. The two negatively-charged carboxylate groups make receptor 3 soluble in water. Electrostatic attraction between negatively charged carboxylate groups of 3 and the positive charge of guanidinium ion together with the preorganized network of the hydrogen-bond acceptor sites of the receptor make the complex of 3 with guanidinium ion to be highly stable even in water. However, receptor 3 does not change any optical properties upon binding guanidinium ions.

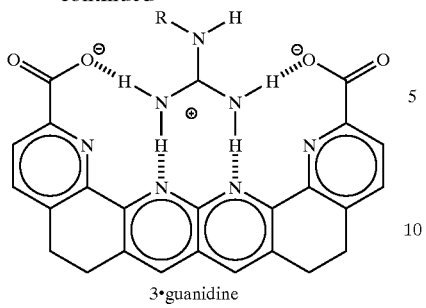

3·guanidine

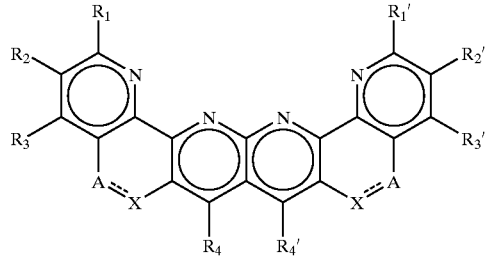

(I)

A rigid U-shaped guanidinium receptor (4) undergoes a small change in absorption spectrum upon complexation to unsubstituted guanidinium ion (Bell et al., *Angew. Chem. Int. Ed. Eng.* 1990, 29, 923–925). The mechanism of this absorption change apparently comes from partial flexibility of the naphthyridine arms in 4. Without guanidinium these arms can flip up and down from the plane of the molecule. Complexation of guanidinium ion partially restricts this motion, resulting rigidification of the chromophore with consequent change in optical properties. However, receptor 4 is restricted by design to bind only to unsubstituted guanidinium ion. In addition, the molecules it is not soluble in water due to lipophilicity of the molecule.

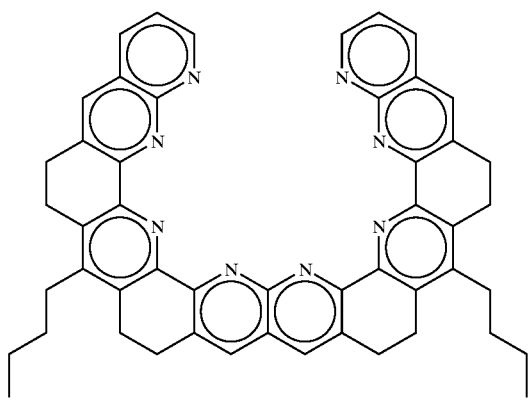

4

From the above examples of urea and guanidinium receptors, it will be readily apparent that currently available compounds lack one or more of the useful properties required for utilization as chemosensors. These properties include aqueous solubility, strong binding to analyte in aqueous solutions and optical signaling of the binding event. In view of these deficiencies, there is a need for compounds that can provide a suitable balance of these properties.

Accordingly, it is an object of the present invention to provide compounds that exhibit these required properties.

SUMMARY OF THE INVENTION

The present invention provides multicyclic aromatic compounds having the formula set forth below:

where $R_1$, $R_2$ and $R_3$ are the same or different and at least one is selected from the group consisting of a hydrophillic substituent, a directly or indirectly linked quencher molecule, a substituted or unsubstituted heterocyclic ring structure, and a combination thereof, with the remainder being hydrogen, where $R_1'$, $R_2'$ and $R_3'$ are the same or different and at least one is selected from the group consisting of a hydrophillic substituent, a substituted or unsubstituted heterocyclic ring structure, a directly or indirectly linked fluorophore, $R_1'$ and $R_2'$ together form a five- or six-membered cyclic ring fused to a substituted or unsubstituted heterocyclic ring structure, and a combination thereof, with the remainder being hydrogen;

where R4 and R4' are the same or different and are selected from the group consisting of hydrogen, a hydrophillic substituent, a substituted or unsubstituted heterocyclic ring structure, a directly or indirectly linked quencher molecule, a directly or indirectly linked fluorophore and a combination thereof, or R4 and R4' together form a five- or six-membered cyclic ring fused to a substituted or unsubstituted heterocyclic ring structure;

where A and A' are the same or different and are selected from the group consisting of carbon, nitrogen, oxygen, sulfur and a combination thereof, where X and X' are the same and different and are a substituted or unsubstituted chain of 0 to 10 atoms selected from the group consisting of carbon, nitrogen, oxygen, sulfur, and a combination thereof;

where $R_1$ and $R_1'$ are not both selected from the group consisting of a carboxy group, a carboxylate and a combination thereof, when $R_2$, $R_2'$, $R_3$, $R_3'$, $R_4$, and $R_4'$ are hydrogen, A and A' are methylene, and X and X' are methylene; and where $R_1$ is not selected from the group consisting of a carboxy group and a carboxylate, when $R_1'$ is a substituted heterocyclic ring structure being a pyridine with substituents other than amines or alcohols.

The present invention also advantageously provides methods of forming complexes with urea, guanidine, mono- or di-substituted alkyl guanidines, derivatives thereof and acid addition salts thereof, which includes:

(a) providing a multicylic aromatic compound having the formula:

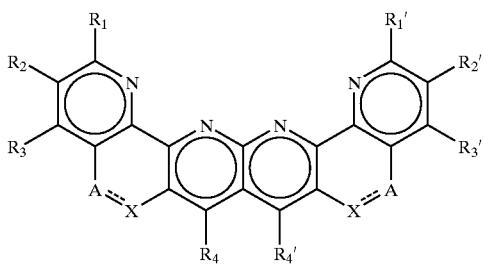

where $R_1$, $R_2$ and $R_3$ are the same or different and at least one is selected from the group consisting of a hydrophillic substituent, a directly or indirectly linked quencher molecule, a substituted or unsubstituted heterocyclic ring structure, and a combination thereof, with the remainder being hydrogen, where $R_1'$, $R_2'$ and $R_3'$ are the same or different and at least one is selected from the group consisting of a hydrophillic substituent, a substituted or unsubstituted heterocyclic ring structure, a directly or indirectly linked fluorophore, $R_1'$ and $R_2'$ together form a five- or six-membered cyclic ring fused to a substituted or unsubstituted heterocyclic ring structure, and a combination thereof, with the remainder being hydrogen;

where $R_4$ and $R_4'$ are the same or different and are selected from the group consisting of hydrogen, a hydrophillic substituent, a substituted or unsubstituted heterocyclic ring structure, a directly or indirectly linked quencher molecule, a directly or indirectly linked fluorophore and a combination thereof, or $R_4$ and $R_4'$ together form a five- or six-membered cyclic ring fused to a substituted or unsubstituted heterocyclic ring structure;

where A and A' are the same or different and are selected from the group consisting of carbon, nitrogen, oxygen and sulfur;

where X and X' are the same and different and are a substituted or unsubstituted chain of 0 to 10 atoms selected from the group consisting of carbon, nitrogen, oxygen, sulfur, and a combination thereof;

where $R_1$ and $R_1'$ are not both selected from the group consisting of a carboxy group, a carboxylate and a combination thereof, when $R_2$, $R_2'$, $R_3$, $R_3'$, $R_4$, and $R_4'$ are hydrogen, A and A' are methylene, and X and X' are methylene; and where $R_1$ is not selected from the group consisting of a carboxy group and a carboxylate, when $R_1'$ is a substituted heterocyclic ring structure being a pyridine with at least one substituent other than an amine or alcohol; and (b) contacting the multicylic aromatic compound with a sample including at least one component selected from the group consisting of urea, thiourea, guanidine, mono- or di-substituted alkyl guanidines, creatine, creatinine, substituted and unsubstituted arginine, substituted and unsubstituted amidine, derivatives thereof and acid addition salts thereof.

DETAILED DESCRIPTION OF THE INVENTION

Figure 1:
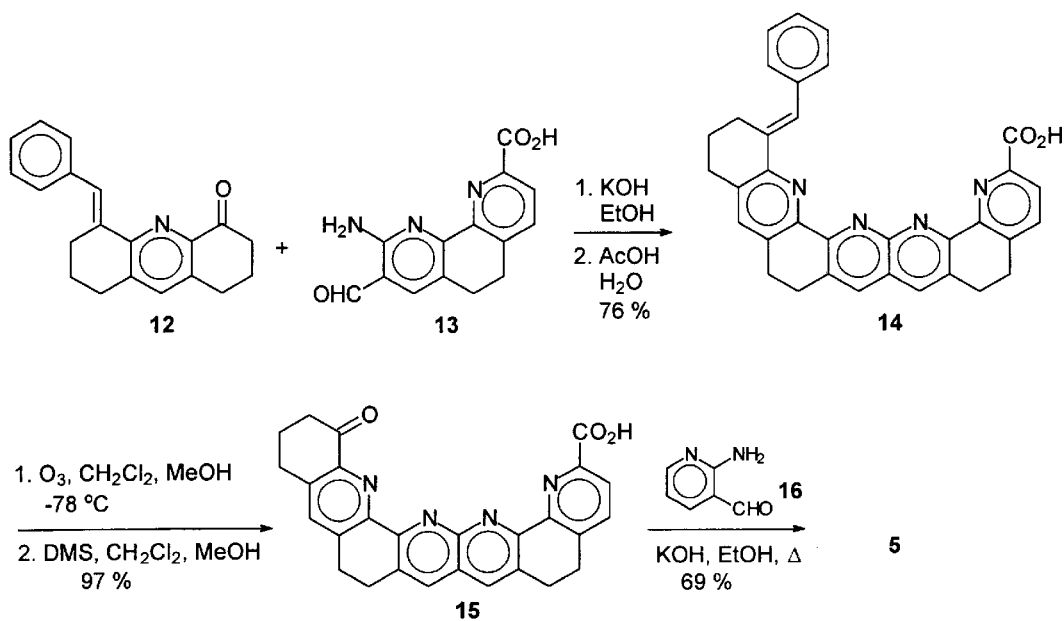
FIG. 1 is a reaction scheme illustrating the synthesis of compound IA of the present invention.

In accordance with the present invention, multicyclic aromatic compounds are provided, which are useful as complexing agents. The compounds of the present invention have the general formula:

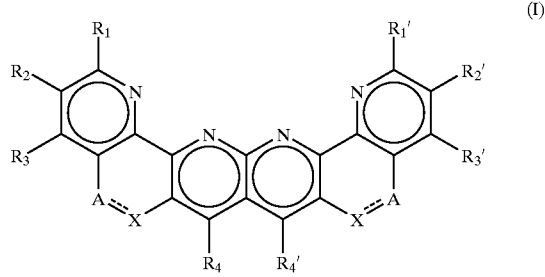

where the substituents are the following:

(a) $R_1$, $R_2$ and $R_3$ are the same or different and at least one of $R_1$, $R_2$ or $R_3$ is a hydrophilic substituent, a directly or indirectly linked quencher molecule, a substituted or unsubstituted heterocyclic ring structure, or a combination thereof, with the remainder being hydrogen;

(b) $R_1'$, $R_2'$ and $R_3'$ are the same or different and at least one of $R_1'$, $R_2'$ and $R_3'$ is a hydrophilic substituent, a substituted or unsubstituted heterocyclic ring structure, a directly or indirectly linked fluorophore, $R_1'$ and $R_2'$ together form a five or six-membered cyclic ring fused to a substituted or unsubstituted heterocyclic ring structure, or a combination thereof, with the remainder being hydrogen;

(c) $R_4$ and $R_4'$ are the same or different and are either hydrogen, a hydrophilic substituent, a substituted or unsubstituted heterocyclic ring structure, a directly or indirectly linked quencher molecule, a directly or indirectly linked fluorophore, a combination thereof or $R_4$ and $R_4'$ together form a five- or six-membered cyclic ring fused to a substituted or unsubstituted heterocyclic ring structure;

(d) A and A' are the same or different and are either carbon, nitrogen, oxygen, sulfur or a combination thereof;

(e) X and X' are the same and different and are either a substituted or unsubstituted chain of 0 to 10 atoms being either carbon, nitrogen, oxygen, sulfur, or a combination thereof;

(f) $R_1$ and $R_1'$ are not a carboxy group, a carboxylate or a combination thereof, when $R_2$, $R_2'$, $R_3$, $R_3'$, $R_4$ and $R_4'$ are hydrogen, A and A' are methylene, and X and X' are methylene; and (g) $R_1$ is not a carboxy group or a carboxylate, when $R_1'$ is a substituted heterocyclic ring structure being a pyridine with substituents other than amines or alcohols.

Hydrophilic substituents to be utilized are any hydrophilic functional groups, with functional groups capable of forming hydrogen bonds being particularly preferred. The hydrophilic functional groups can be directly attached to the ring structure or can be attached to the ring structure by short carbon chain with one to ten carbons being preferred, with one to three carbons being more preferred. The carbon chain can also be substituted or unsubstituted, saturated or unsaturated, and contain small ring structures (e.g., cyclobutane) or heteroatoms (e.g., sulfur, oxygen, and nitrogen). However, to provide ideal positioning of potential hydrogen bonding sites for an analyte and water solubility, it is preferable to directly attach the hydrophilic substituent to the ring structure. Representative example of hydrophilic substituents to be utilized include, but are not limited to, the following functional groups: alcohols, amines, carboxylic acids, carboxylates, amides, sulfamides, sulfonic acids, sulfonates, sulfates, esters, thiol esters, ethers, thiols, thiolates, thioethers, and combinations thereof. Particularly preferred groups are primary alcohols and primary amines due to their potential for hydrogen bonding. In one embodiment $R_1$, $R_2$, $R_3$ or $R_4$ is a hydrophilic substituent and the corresponding substituent $R_1$, $R_2'$, $R_3'$, or $R_4'$ is a different hydrophilic substituent. For example, if $R_2$ is a carboxyl group or a carboxylate, then $R_2'$ is a hydrophilic substituent other than a carboxylic acid or a carboxylate, such as an amide. Moreover, in accordance with the invention, $R_1$ and $R_1'$ are not a carboxy group, a carboxylate or a combination thereof, when $R_2$, $R_2'$, $R_3$, $R_3'$, $R_4$ and $R_4'$ are hydrogen, A and A' are methylene, and X and X' are methylene. A compound that would fall within this description if $R_1$ and $R_1'$ are a carboxylate is the "arginine cork."

Quencher molecules and fluorophors to be utilized are known in the art as illustrated by U.S. Pat. No. 5,464,587, which is incorporated herein by reference. "Quencher molecules" are compounds that have substituents being strong electron acceptors or donors. Generic example of these types substituents are nitro-groups, cyano-groups, amino-groups, methoxy-groups, viologenes, halides, and pseudohalides. Specific examples of these substituents include, but are limited to, nitrophenylmethyl, dinitrobenzyl, diethylamino, dimethylamino, dimethoxy, phenethyl groups. Fluorophors are compounds capable of fluorescence and typically fall into the class of polycyclic and heterocyclic aromatics. Representative examples of these compounds include, but are not limited to, 2-aminoanthracene, rubrene, decacyclene, and metal ion complexes with heterocyclic ligands such as trisruthenium-bipyridyl or tris-ruthenium-phenanthroline. In a preferred embodiment of the invention, either $R_1$, $R_2$, $R_3$, or $R_4$ is a quencher molecule while either $R_1'$, $R_2'$, $R_3'$, or $R_4'$ is a fluorophore, with $R_1$ and $R_1'$ being more preferred. One preferred combination of a quencher and fluorophore is 4-dimethylamino-2,5-dimethoxyphenyl and a substituted 4-amino-1,8-naphthalimidyl, respectively.

As described above, the quenchers and fluorophors can be directly or indirectly linked to the ring structure. In this context, the term "directly" means that the quencher or fluorophore is attached to the ring structure without the aid of a linker, while "indirectly" means that the quencher or fluorophore is attached to the ring structure with a linker. A "linker" in this context means any type small molecule extraneous to the structure of the quencher or fluorophore that acts as a bridge to the ring structure. Examples of moieties that can act as "linkers" are well known in the art especially with the immobilization of compounds to various substrates such as polystyrene beads. Preferred examples include, but are not limited to, amides, esters, ethers, and disulfides optionally with a short carbon chain as described above for the hydrophilic substituents.

Heterocyclic ring structures for the compounds of the invention include any water-soluble heterocyclic structure, with monocyclic and bicyclic structures being preferred. Representative examples of heterocyclic ring structures to be utilized include, but are not limited to, pyridines, pyrimidines, naphthyridines and combinations thereof. In additional embodiments, the heterocycles can be substituted, with the hydrophilic substituents described above being preferred. Examples are pyridines, pyrimidines, and naphthyridines substituted with at least one primary alcohol, primary amine or a combination of the two, which provide additional sites for hydrogen bonding. However, in accordance with the invention, $R_1$ is not a carboxy group or a carboxylate, when $R_1'$ is a substituted heterocyclic ring structure being a pyridine with substituents other than amines or alcohols. Stated otherwise, when $R_1$ is a carboxy group or a carboxylate, and $R_1'$ is a substituted pyridine, the substituents are only amines or alcohols.

In accordance with the present invention, A, A', X and X' are variable to alter the two non-aromatic rings in formula (I). As previously described, A and A' are the same or different and can be either carbon, nitrogen, oxygen, sulfur, or a combination thereof, such as a carbonyl. X and X' are same and different and can be either a substituted or unsubstituted chain of 0 to 10 atoms being either carbon, nitrogen, oxygen, sulfur, or a combination thereof. As will be readily apparent to one skilled in the art, if X or X' contain zero (0) atoms, a five-membered ring is provided. Likewise, if X or X' contains a single atom, a six-membered ring is provided. In a preferred embodiment, X or X' contains zero to two atoms which provide the non-aromatic rings of formula (1) with either a five-membered, a six-membered or a seven-membered cyclic structure. Moreover, if X or X' are two or more atoms, the chain can be saturated or unsaturated. Additionally, the invention provides compounds that can have a double bond between X and A, and X' and A', as indicated by the dashed bonds in formula (I).

In a particular embodiment, the present invention provides compounds where $R_1$ is carboxylic acid or a carboxylate directly attached to the ring structure of formula (I), and $R_1'$ and $R_2'$ form a five- or six-membered cyclic ring (six membered preferred) fused to a substituted or unsubstituted naphthyridine. The naphthyridine group is preferably situated (i.e., fused to the five- or six-member ring) so that the nitrogen in the naphthyridine group closest to the ring structure (or scaffold) of formula (I) is in a 1,4-syn orientation to the nitrogen in the pyridine ring to which $R_1'$ is attached. A particularly preferred example of this embodiment is a compound having the formula:

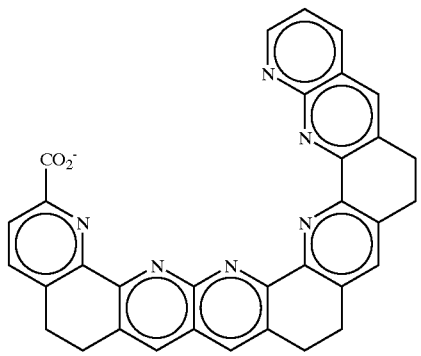

(IA)

Another particularly preferred example of this embodiment is a compound having the formula:

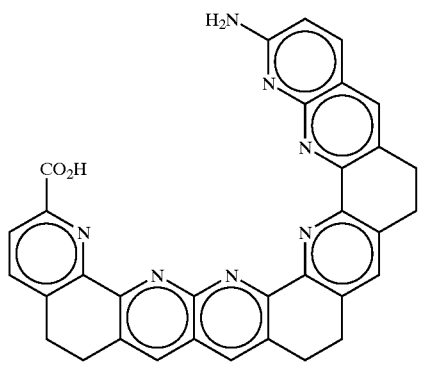

(IB)

In another particular embodiment, the present invention provides compounds where $R_1$ is carboxylic acid or a carboxylate, and $R_1'$ is substituted or unsubstituted pyridine. One particularly preferred example of this embodiment is a compound having the formula:

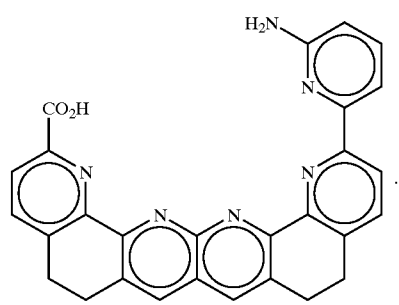

(IC)

Alternatively, $R_1$ and $R_1'$ can both be either a substituted pyridine, an unsubstituted pyridine, or a combination thereof.

In an additional particular embodiment, the present invention provides compounds where $R_1$ is a carboxylic acid or a carboxylate, and $R_1'$ is a substituted or an unsubstituted pyrimidine. One particularly preferred example is a compound having the formula:

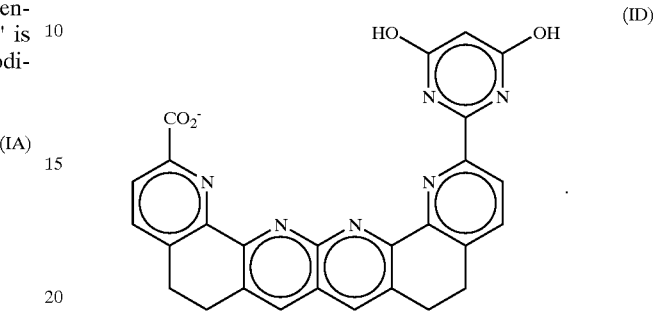

(ID)

Alternatively, $R_1$ and $R_1'$ can both be either a substituted pyrimidine, an unsubstituted pyrimidine, or a combination thereof.

In another particular embodiment, the present invention provides compounds where $R_1$ is a indirectly linked quencher molecule and $R_1'$ is an indirectly linked fluorophor. More preferred is where the quencher molecule and the fluorophor are each linked to the ring structure through separate amides via direct attachment to the n-terminus of the amide (i.e., the nitrogen atom). One particular example is a compound having the formula:

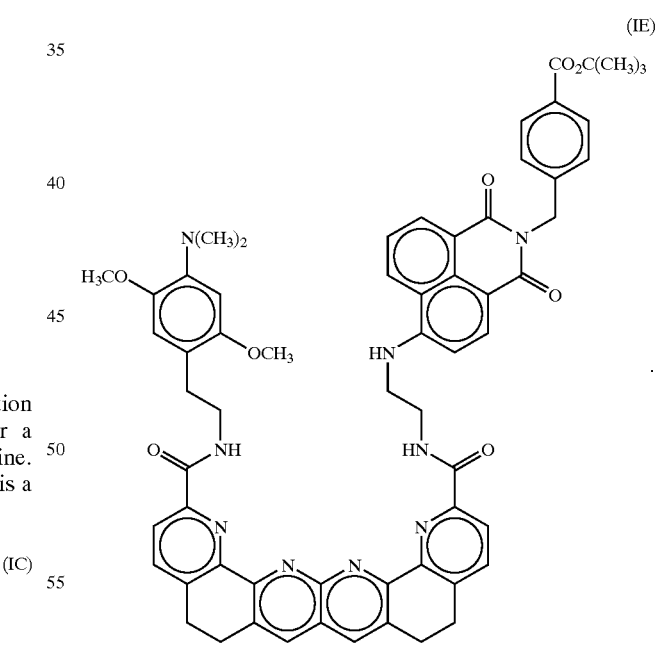

(IE)

The compounds of the present invention are particularly useful for forming complexes with urea, thiourea, guanidine, mono- or di-substituted alkyl guanidines, creatine, creatinine, substituted and unsubstituted arginine, substituted and unsubstituted amidine, derivatives thereof and acid addition salts thereof. The compounds of the present invention, therefore, can be advantageously utilized in assays and sensors where complexation of an analyte such as urea or guanidine is desired.

Moreover, it will be apparent to one skilled in the art from the teachings of the invention that the affinity of the compounds can be tailored to a specific analyte through the choice of substituents. For example, the compounds of the invention can synthesized to provide at least 5 or 6 potential sites for hydrogen bonding. An example of a compound having 6 potential hydrogen bonding sites is where $R_1$ and $R_1'$ are the same and are heterocyclic structures such as amine or alcohol substituted pyridines or pyrimidines. Likewise, the protonation of substituents (e.g., carboxylic acids or the nitrogens in the naphthyridine group) can affect the affinity of the compound for a specific analyte. Protonation will affected by such parameters as the pH of the solution in which the compound is dissolved. These and other parameters can be easily ascertained by one skilled in the art from the teachings of the invention.

In view of the above, the present invention also provides a method of complexing urea, guanidine, mono- or di-substituted alkyl guanidines, derivatives thereof and acid addition salts thereof. In accordance with the method, a multicyclic aromatic compound having formula (I) is provided. The multicyclic aromatic compound is then contacted with a sample containing a component being urea, guanidine, a mono- or di-substituted alkyl guanidine, a derivatives thereof or an acid addition salt thereof in which the compound of the present invention and the component in the sample form a complex. Additionally, the method includes measuring changes in optical signaling for the compounds of the invention due to complex formation. "Optical signaling" in this context means any type of optical property for the compound that can be measured, such as light absorption or emission (i.e., luminescence). Thus, measuring a change in optical signaling entails measuring the optical signal before complex formation and after complex formation. A preferred optical signal for use in the method of the invention is luminescence with fluorescence being more preferred. Once a change in optical signaling is measured, the method further includes correlating the change in optical signaling to the concentration of the component (i.e., analyte) in the sample following techniques known in the art thus providing a method of detecting and quantitating an analyte in a sample. As will be apparent to one skilled in the art, the optical signal provided by the compounds of the invention will vary with the choice of substituents and level of protonation. However, these parameters can be easily determined by one skilled in the art.

The compounds of the present invention can be synthesized following techniques known in the art as illustrated by the examples set forth below. Accordingly, one skilled in the art can synthesize the compounds of the invention following the teachings of the examples.

EXAMPLES

The following non-limiting examples illustrate the synthesis, characterization and utility of the multicyclic aromatic compounds of the present invention.

Example 1

Synthesis of Compound IA—(5,6,9,10,13,14-Hexahydro-15(12H)-benzo[b][1,10]phenanthrolino[3,2-j][1,10]phenanthrolinone-2-carboxylic acid, potassium salt )

Briefly, compound IA (5) was synthesized starting from aminoaldehyde (intermediate 13) (Bell et al., *Angew. Chem., Int. Ed. Engl.*, 1999, 38, 2543–2547). Friedländer condensation of acridinone (intermediate 12) with aminoaldehyde 13 was carried out in absolute ethanol. KOH was used as a base for this reaction with controlled basicity (pH 10) to obtain the ethanol-insoluble potassium salt of benzylidene (intermediate 14). A simple vacuum filtration afforded an 83% yield of relatively pure compound. The potassium salt of 14 was converted to the acid form with acetic acid at pH 5–6. Addition of acetic acid caused a massive precipitation of yellow compound 14. The next step involves oxidation of the benzylidene double bond in 14 with ozone. This reaction was carried out in 5:1 (v/v) mixture of dichloromethane/methanol at low temperature (−78° C.). The completion of the reaction was monitored by color change from amber to blue, which indicates the presence of excess ozone in the solution. After that, the intermediate ozonide was quenched with dimethyl sulfide. The crude ketone (intermediate 15), which resulted after evaporation of the solvent mixture, was conveniently purified by suspending it in a small amount of chloroform with the aid of ultrasonication, which dissolved impurities and left pure 15 as a solid. However, only about a 40% yield of 15 was obtained this way. To recover the rest of the compound, the mother liquor from the first purification was triturated with diethyl ether. This caused precipitation of remaining 15, which in combination with the first crop resulted in almost quantitative yield (97%) together with good purity by NMR. Condensation of ketoacid 15 with 2-amino-3-pyridinecarboxaldehyde ( intermediate 16) (Majewicz et al., *J. Org. Chem.* 1974, 39, 720) in ethanol with KOH as a base at pH 9–10 afforded potassium salt of compound IA 5, which was precipitated by trituration of the concentrated reaction solution with ether. A reaction scheme illustrating the synthesis of compound IA is shown in FIG. 1. The synthesized compounds were analyzed by $^1$H and $^{13}$C NMR using a General Electric QE-300 NMR spectrometer operating at 300 MHz and on a Varian Unity spectrometer operating at 500 MHz, respectively. Mass spectra were taken using a Hewlett-Packard 59970.

A. Synthesis of intermediate 14—(15-Benzylidene-5,6,9,10,12,13,14,15-octahydrobenzo[b][1,10]phenanthrolino[3,2-j][1,10]phenanthroline-2-carboxylic acid)

A 500-mL round-bottomed flask equipped with a stirring bar, condenser and nitrogen gas inlet was charged with 1.18 g (4.38 mmol) of 5,6-dihydro-9-amino-8-[1,10]phenanthrolinecarboxaldehyde-2-carboxylic acid (13), 1.27 g (4.38 mmol) of 5-benzylidene-2,3,5,6,7,8-hexahydro-4(1H)-acridinone (12) and 250 mL of ethanol. The mixture was heated to boiling and then KOH solution in methanol was added dropwise to achieve pH 10 (approximately 1.8 mL of 1.055 N KOH solution was required). The resulting mixture was heated under reflux, under nitrogen for 3 days. Then the solvent was partially removed by rotary evaporation to 70 mL, 400 mL of ether was added and the mixture was cooled in a freezer over a period of 12 h. The precipitate was collected by vacuum filtration, washed with 10 mL of ether and dried under vacuum (0.1 mm) to give 2.04 g of 14 as a potassium salt. The crude product was suspended in 50 mL of water and acetic acid was added to achieve pH 5–6. The mixture was cooled in a refrigerator over a period of 5 h, then the precipitate was collected by vacuum filtration, washed with 5 mL of ice cold water and dried under vacuum (0.1 mm) over $P_2O_5$ over a period of 24 h. to give 1.73 g (76%) of acid 14. $^1$H NMR (300 MHz, TFA-$d_1$, 35 mM): δ10.95 (s, 1H, H16), 10.59 (s, 1H, H8), 10.43 (d, J=8.05 Hz, 1H, H4), 10.20 (s, 1H, H7), 10.11 (d, J=8.05 Hz, 1H, H3), 9.70 (s, 1H, H11), 9.45 (m, 5H, Ph), 5.48 (m, 4H, H5,6), 5.39 (m, 4H, H9,10), 5.08 (m, 4H, H12,14), 4.01 (q, 6.22 Hz, 2H, H13) $^{13}$C NMR (126 MHz, D$_2$O): δ169.6, 152.7, 152.3, 151.6, 148.3, 148.1, 148.0, 145.9, 145.1, 143.9, 142.5, 140.6, 140.4, 140.3, 140.2, 139.1, 137.8, 136.2, 132.4, 132.1, 130.8, 130.1, 128.2, 30.5, 28.4, 27.5, 27.4, 27.2, 26.3, 23.1. FAB-MS, m/z (rel. intensity): 523.4 (M+1, 100), 479.4 (81). For microanalysis 50 mg of crude 14 was dissolved in 3 mL of hot DMSO, then 3 mL of water was added and cooled to 0° C. The precipitate was collected by vacuum filtration, washed with water (4×2 mL) and dried under vacuum (0.1 mm, 70° C.) for 2 days to give 24 mg of pure 14, mp 248–250° C. with dec. Anal. Calcd for C$_{34}$H$_{26}$N$_4$O$_2$.0.5 H$_2$O: C, 76.80; H, 5.12; N, 10.54%. Found: C, 77.12; H, 4.88; N, 10.23%.

B. Synthesis of Intermediate 15—(5,6,9,10,13,14-Hexahydro-15(12H)-benzo[b][1,10]phenanthrolino [3,2-j][1,10]) phenanthrolinone-2-carboxylic acid)

A 1-L round-bottomed flask equipped with a magnetic stirring bar was charged with 1.52 g (2.91 mmol) of 15-benzylidene-5,6,9,10,12,13,14,15-octahydrobenzo[b][1,10]phenanthrolino[3,2-j][1,10]phenanthroline-2-carboxylic acid (14), 560 mL of dichloromethane and 120 mL of methanol. The solution was cooled to −78° C. in a dry ice/acetone bath and a stream of O$_3$/O$_2$ was bubbled through the solution until it became distinctive greenish-blue. The solution was purged by bubbling nitrogen gas for 1 h, then 0.85 mL (11.64 mmol) of dimethylsulfide was added via syringe. The solution was warmed to room temperature overnight, then the solvent was removed by rotary evaporation and the remaining residue was suspended in 6 mL of chloroform with ultrasonication. The precipitate was collected by vacuum filtration, washed with 1 mL of cold chloroform and dried under vacuum (0.1 mm) to give 0.56 g of the first crop of 15. To the mother liquor 50 mL of ether was added and the mixture was cooled in a freezer over 2 h. The precipitate was collected by vacuum filtration, washed with 5 mL of cold ether and dried under vacuum (0.1 mm) to give 0.70 g of the second crop of 15. Both crops yielded 1.26 g (97%) of 15. For microanalysis a sample was recrystallized from a mixture of DMSO/H$_2$O (1:1) and dried under vacuum (0.1 mm, RT) for 3 days; mp 255–260° C. with dec. $^1$H NMR (300 MHz, DMSO-d$_6$): δ13.0 (br., 1H, OH), 8.26 (s, 2H, H7,8), 8.02 (d, J=7.7 Hz, 1H, H3), 7.95 (d, J=8.1 Hz, 1H, H4), 7.8 (s, 1H, H11), 3.13 (br., 10H, H5,6,9,10,14), 2.71 (br., 2H, H12), 2.07 (br., 2H, H13); $^{13}$C NMR (125.7 MHz, DMSO-d6): δ196.1, 166.2, 154.4, 154.0, 153.6, 151.6, 150.4, 149.7, 147.6, 147.3, 142.1, 139.4, 137.7, 137.5, 134.7, 134.6, 133.4, 133.3, 125.1, 122.6, 28.4, 26.8, 26.7, 22.2. IR (KBr): ν3568 (w), 3394(bw), 2944(w), 1711 (s), 1686(s), 1655(w), 1612(w), 1591(m), 1571(w), 1561 (w), 1534(w), 1461(m), 1439(w), 1420(w), 1396(w), 1350 (s), 1262(w), 1209(m), 1170(m), 1068(w) 1027(w), 1001 (w), 973(w), 931(w), 901(w), 812(w), 780(w), 756(w), 736(w), 713(w), 660(w) 621(w), 601(w), 547(w). FAM-MS, m/z (rel. intensity): 449.3 (M+1, 100), 405.3 (63). Anal. Calcd for C$_{27}$H$_{20}$N$_4$O$_3$.2 H$_2$O: C, 66.92; H, 4.99; N, 11.56%. Found: C, 67.20; H, 4,84; N, 11.64%.

C. Synthesis of Compound IA—(5,6,9,10,12,13-Hexahydro[1,10]phenanthrolino[2,3-b]pyrido[2'3':2,3]quino[7,8-j][1,10]phenanthroline-2-carboxylic acid, potassium salt)

A 250-mL round-bottomed flask equipped with a stirring bar, condenser and nitrogen gas inlet was charged with 0.282 g (0.63 mmol) of 5,6,9,10,13,14-hexahydro-15(12H)-benzo[b][1,10]phenanthrolino[3,2-j][1,10]phenanthrolinone-2-carboxylic acid (15), 0.077 g (0.63 mmol) of 2-amino-3-pyridinecarboxaldehyde (16) and 120 mL of ethanol. The mixture was heated to boiling and then KOH solution in methanol was added dropwise to achieve pH 9–10 (approximately 20 drops of 15% KOH solution was required). The resulting mixture was heated under reflux, under nitrogen for 3 days. Then the solvent was partially removed by rotary evaporation to 20 mL and 150 mL of ether was added to cause precipitation. The mixture was centrifuged for 10 min and most of the solvent was decanted away from the solid. The remaining suspension was subjected to vacuum filtration. The precipitate was washed with 5 mL of ether and dried under vacuum (0.1 mm) to give 0.247 g (69%) of crude potassium salt 5 (compound IA). Then 0.10 g of 5 was suspended in 7 mL of water with the aid of ultrasonication (30 min), and 2 N aq.HCl was added to reach pH 5–6. The precipitate was collected by vacuum filtration and dried under vacuum (0.1 mm, RT) over a period of 24 h to give 0.09 g of acid 5 (compound IA). The crude product was dissolved in 3.0 mL of hot DMSO, then 5.0 mL of water was added and cooled in an ice bath. The precipitate was collected by vacuum filtration, washed with water (4×2 mL) and dried under vacuum (0.1 mm, RT) over a period of 2 days to give 0.05 g of purified acid 5. $^1$H NMR (300 MHz, TFA-d$_1$): δ11.30 (d, J=8.43 Hz, 1H), 11.09 (s, 1H), 10.93 (s, 1H), 10.85 (s, 1H), 10.72 (s, 1H), 10.63 (d, J=8.06 Hz, 1H), 10.35 (m, 3H), 5.55 (br. 6H); $^{13}$C NMR (75.5 MHz, TFA-d$_1$): δ152.6, 152.0, 151.1 (=3C), 150.7 (=2C), 149.7 (=2), 147.6 (=2C), 147.5, 147.4, 146.5, 146.1, 144.1, 143.9, 143.7, 142.4, 142.0, 139.7, 139.6, 139.0, 132.5, 128.8, 128.5, 127.0, 27.5 (=2C), 27.4 (=4C). FAB-MS, m/z (rel. intensity) (potassium salt 5): 573.3 (M+1, 38), 529.4 (100), 443.4 (42), 345.2 (40).

Example 2

Synthesis of Compound IB—(17-Amino-5,6,9,10,12,13 -hexahydro[1,10]phenanthrolino[2,3-b]pyrido [2'3':2,3]quino[7,8-j][1,10]phenanthroline-2-carboxylic acid, potassium salt)

Figure 2:
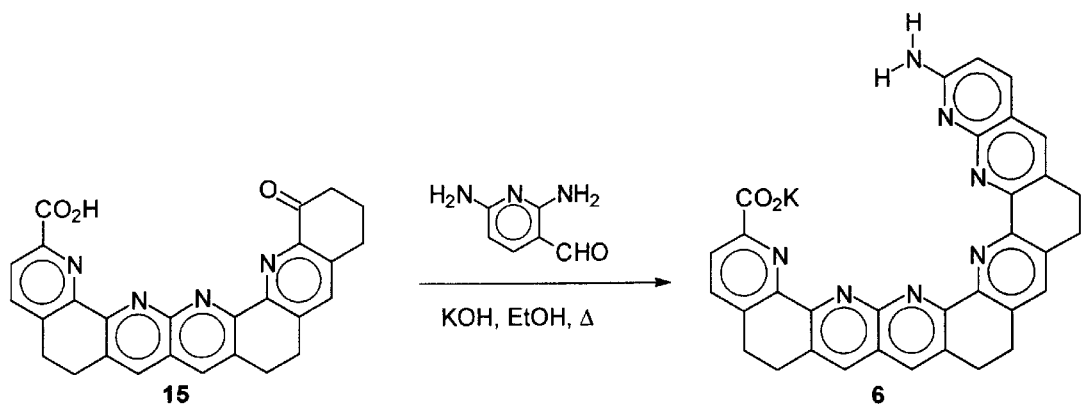
FIG. 2 is a reaction scheme illustrating the synthesis of compound IB of the present invention.

Following the reaction scheme shown in FIG. 2, a 250-mL round-bottomed flask equipped with a stirring bar, condenser and nitrogen gas inlet was charged with 0.282 g (0.63 mmol) of 5,6,9,10,13,14-hexahydro-15(12H)-Benzo[b][1,10]phenanthrolino[3,2-j][1,10]phenanthrolinone-2-carboxylic acid (15), 0.086 g (0.63 mmol) of 2,6-diamino-3-pyridinecarboxaldehyde and 120 mL of ethanol. The mixture was heated to boiling and then KOH solution in methanol was added dropwise to achieve pH 10. The resulting mixture was heated under reflux, under nitrogen for 4 days. Then the solvent was partially removed by rotary evaporation to 20 mL and 150 mL of ether was added to cause precipitation. The mixture was centrifuged for 10 min and most of the solvent was decanted away from the solid. The remaining suspension was subjected to vacuum filtration. The precipitate was washed with 5 mL of ether and dried under vacuum (0.1 mm) to give 0.20 g of a mixture containing receptor 6 (compound IB) and unreacted intermediate 15. FAB-MS: (potassium salt 6) 588.3 (M+1); (potassium salt 15) 487.2 (M+1).

Example 3

Synthesis of Compound IC—5,6,9,10-Tetrahydro-13-(2-aminopyridin-6-yl)[1,10]phenanthrolino [2,3-b][1,10]phenanthroline-2-carboxylic acid Briefly, receptor 8 (compound IC) was synthesized from a ketoacid (intermediate 17). The carboxylic group in 17

Figure 3:
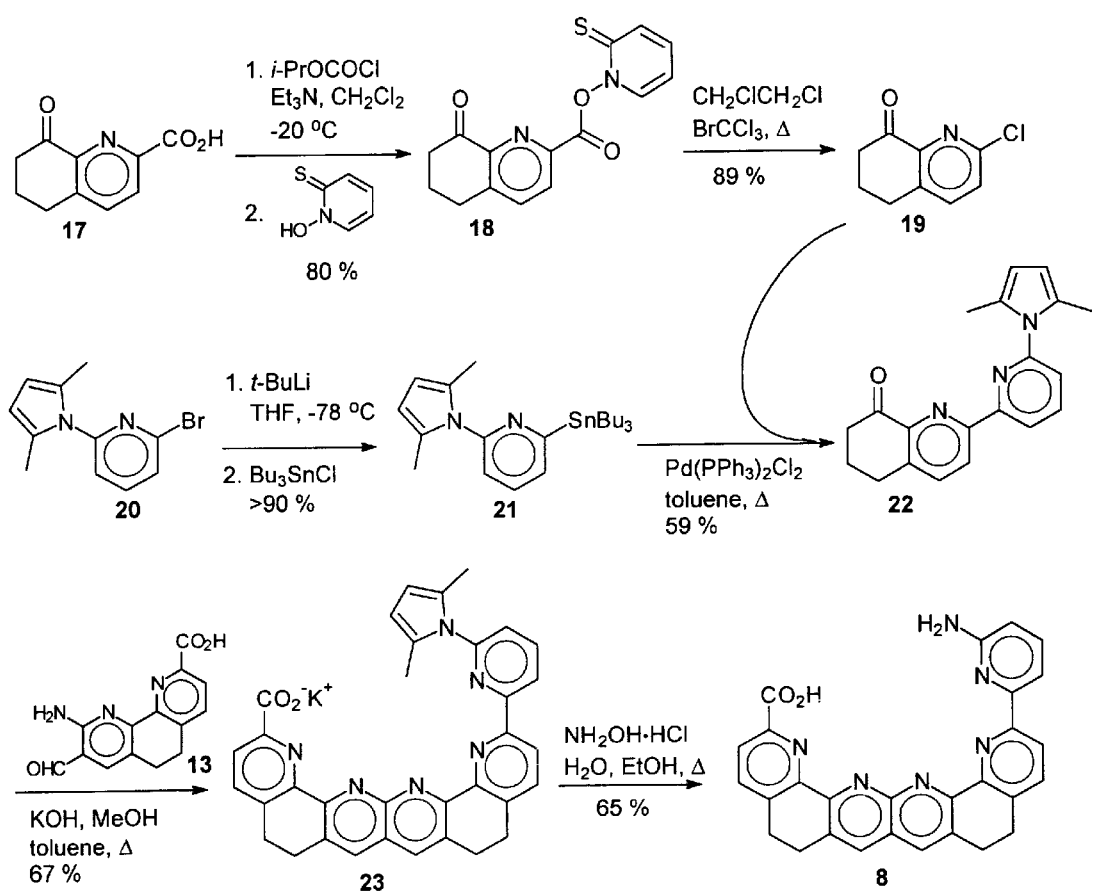
FIG. 3 is a reaction scheme illustrating the synthesis of compound IC of the present invention.

(Bell et al., *Angew. Chem., Int. Ed. Engl.,* 1999, 38, 2543–2547) was replaced with a halogen by means of the Barton reaction (Barton et al., *Tetrahedron* 1985, 41, 3901–3924). However, the commonly used conditions for one pot transformation gave poor yields of halogenated product. When this reaction was done in two steps with isolation of the intermediate 18, chloride 19 was obtained in 71% overall yield for two steps. First, the carboxylic group in 17 was activated with isopropylchloroformate in dichloromethane at −20° C. Then 2-mercaptopyridine-N-oxide was introduced to give ester 18 with an N—O bond that is sensitive to thermolysis. The work-up of the reaction mixture and isolation of 18 was done fast at temperatures below 25° C., which afforded 18 in 80% yield. Ester 18 was heated under reflux in a mixture of $BrCCl_3$ and $CH_2ClCH_2Cl$ for several hours, which afforded pure chloride 19. For asymmetric palladium mediated coupling, alkyltin component 21 was prepared from bromide 20 by metal-halogen exchange with t-BuLi, followed by exchange of lithium with tributyltin chloride. The next step involves coupling between 21 and 19. The best yields of desired product 22 were obtained when 0.1 eq. of palladium catalyst was used together with an excess of tin component 21 (1.5–2 eq.). With these conditions product 22 can be isolated in 59% yield. Condensation of ketone 22 with aminoaldehyde 13 in a methanol/toluene mixture with KOH as a base provided potassium salt 23 in 67% yield. Hydrolysis of the dimethylpyrrole group in 23 with 20 equivalents of hydroxylamine hydrochloride receptor 8 was isolated in 65% yield. A reaction scheme illustrating the synthesis of compound IC is shown in FIG. 3. The synthesized compounds were analyzed by $^1H$ and $^{13}C$ NMR, and Mass Spectrometry as in Example 1.

A. Synthesis of Intermediate 20—(2-Bromo-6-(2,5-dimethyl-1H-pyrrol -1-yl)pyridine)

A 1-L round-bottomed flask equipped with a Dean-Stark head, condenser, nitrogen gas inlet and a magnetic stirring bar was charged with 116.2 g (0.672 mol) of 2-amino-6-bromopyridine (Johnson et al., *J. Org. Chem.* 1962, 27,2473–2478), 80.5 g (0.705 mol) of acetonylacetone (ACROS, 97%), 5 mL of acetic acid and 500 mL of benzene. The mixture was heated under reflux under nitrogen over a period of 48 h. Then the mixture was cooled to room temperature, washed with 300 mL of sat. $NaHCO_3$, then with 300 mL of sat. NaCl and dried over $Na_2SO_4$ (10 g). Then the mixture was concentrated to 100 mL and cooled in a refrigerator over a period of 12 h. The precipitated crystals were collected by vacuum filtration and dried under vacuum (0.1 mm) over a period of 12 h to give 120.9 g (72%) of 20; mp107–109° C. $^1H$ NMR (300 MHz, $CDCl_3$): δ7.68 (dd, J1=8.1 Hz, J2=7.7 Hz, 1H, H4), 7.48 (d, J=8.1 Hz, 1H, H3), 7.18 (d, J=7.7 Hz, 1H, H5), 5.89 (s, 2H, H8), 2.16 (s, 6H, $CH_3$); $^{13}C$ NMR (300 MHz, $CDCl_3$): δ151.6, 140.4, 139.8, 128.5 (=2C), 126.3, 120.1, 107.5 (=2C), 13.2 (=2C). EI-MS (70 eV, quadrupole), m/z (rel. intensity): 252 (M+2, 96), 251 (M+1, 92), 250 (M+, 100), 249 (80), 237 (36), 235 (36), 169 (22), 156 (37), 94 (62). Anal. Calcd for $C_{11}H_{11}BrN_2$: C, 52.61; H, 4.42; N, 11.15%. Found: C, 52.46; H, 4.40; N, 11.21%.

B. Synthesis of Intermediate 18—(6,7-Dihydro-2-(2-pyridinethione-N-oxycarbonyl)-8(5H)-quinolinone)

A 1-L 2-necked round-bottomed flask equipped with a nitrogen gas inlet, a 200 mL pressure equilizing addition funnel and a stirring bar was charged with 16.80 g (87.9 mmol) of 6,7-dihydro-8(5H)-quinolinone-2-carboxylic acid (17), 300 mL of $CH_2Cl_2$ and 10.4 g (14.3 mL, 103 mmol) of triethylamine. The flask was purged with nitrogen gas and the top of addition funnel was closed with a septum. The mixture was stirred and cooled to −20° C. The addition funnel was charged with 100 mL (100 mmol) of 1M solution of isopropylchloroformate in toluene (Aldrich) via cannula under nitrogen. Then the solution of isopropylchloroformate in toluene was added dropwise to the reaction mixture over a period of 1 h at −20° C. The mixture was stirred below −10° C. for 0.5 h. The addition funnel was charged with a solution of 13.35 g (105 mmol) of 2-mercaptopyridine-N-oxide (Aldrich, 99%) in 100 mL of $CH_2Cl_2$ via syringe. The solution of 2-mercaptopyridine-N-oxide was added dropwise over a period of 1 h at −20° C. The stirring was continued for 1 h at −10° C., then the mixture was refrigerated for 12 h. The mixture was washed with 200 mL of sat. $NaHCO_3$ and dried over $Na_2SO_4$ (5 g). The solvent was evaporated under reduced pressure (1–3 mm) at <15° C. To the resulting residue, 60 mL of methanol was added and the mixture was briefly ultrasonicated (2–3 min) to cause crystallization and cooled in a freezer for 3 h. The precipitate was collected by vacuum filtration, washed with 10 mL of cold methanol and dried under vacuum (0.1 mm) over $P_2O_5$ for 15 h to give 21.14 g (80%) of product 18, which was immediately used in the next step. $^1H$ NMR (300 MHz, DMSO-$d_6$): δ8.50 (d, J=6.6 Hz, 1H, H9), 8.30 (d, J=8.1 Hz, 1H, H3), 8.13 (d, J=8.1 Hz, 1H, H4), 7.60 (d, J=8.8 Hz, 1H, H12), 7.46 (dd, $J_1$=6.9, $J_2$=7.3 Hz, 1H, H11) 6.98 (dd, 1H, H10), 3.11 (t, J=5.9 Hz, 2H, H7), 2.76 (t, J=6.4 Hz, 2H, H5), 2.10 (m, 2H, H6).

C. Synthesis of Intermediate 19—(2-Chloro-6,7-dihydro-8(5H)-quinolinone)

A 2-L round-bottomed flask equipped with a stirring bar, condenser and nitrogen gas inlet was charged with 21.14 g (70.39 mmol) of 6,7-dihydro-2-(2-pyridinethione-N-oxycarbonyl)-8(5H)-quinolinone (18), 700 mL of 1,2-dichloroethane and 100 mL of bromotrichloromethane. The mixture was heated under reflux under nitrogen for 26 h. Then the solvent was evaporated under reduced pressure (14 mm) at 50° C. The resulting viscous oil was dissolved in 10 mL of chloroform and passed through a silica gel plug (100 g) with 750 mL of $CHCl_3$/MeOH (98/2) mixture. The solvent was evaporated and the resulting residue was dissolved in 35 mL of ethyl acetate. To the formed solution 250 mL of hexane was added and the mixture was cooled in a freezer for 12 h. The pale-yellow precipitate was collected by vacuum filtration, washed with cold hexane (2×10 mL) and dried under vacuum to give 11.42 g (89%) of 19; mp 126–128° C. (Lit.(Zimmerman et al., *J. Am. Chem. Soc.* 1991, 113, 183–196) 127–129° C.). $^1H$ NMR (300 MHz, $CDCl_3$): δ7.63 (d, J=8.1 Hz, 1H, H4), 7.41 (d, J=8.1 Hz, 1H, H3), 3.01 (t, J=6.0 Hz, 2H, H7), 2.80 (t, J=6.6 Hz, 2H, H5), 2.20 (m, 2H, H6); $^{13}C$ NMR (76 MHz, $CDCl_3$): δ194.6, 150.5, 147.8, 140.3, 139.3, 127.9, 39.2, 28.4, 22.3. EI-MS (70 eV, quadrupole), m/z (rel. intensity): 181 (M+, 91), 153 (40), 127 (71), 125 (100), 116 (21), 90 (40), 63 (38), 55 (62). For microanalysis a sample was recrystallized from ethyl acetate and dried under vacuum (0.1 mm, RT) for 2 days. Anal. Calcd for $C_9H_8ClNO$: C, 59.52; H, 4.44; N, 7.71%. Found: C, 59.48; H, 4.12; N, 7.88%.

D. Synthesis of Intermediate 21—(2-Tri-n-butylstannyl-6-(2,5-dimethyl-1H-pyrrol-1-yl)pyridine)

A 1-L single-necked round-bottomed flask equipped with a magnetic stirring bar and 200-mL pressure equalizing addition funnel was charged with 20.0 g (79.6 mmol) of 2-bromo-6-(2,5-dimethyl-1H-pyrrol-1-yl)pyridine (20) and 500 mL of anhydrous THF. The top neck of the addition funnel was closed with a rubber septum to which a needle leading to the nitrogen gas line was inserted. The mixture was cooled to −78° C. by means of dry ice/acetone bath. The addition funnel was charged with 111.5 mL (167.2 mmol) of 1.5 M solution of t-butyl lithium in pentane (ACROS), which was then added dropwise to the reaction mixture over a period of 2 h. The mixture was stirred for an additional 1 h. The addition funnel was charged with 27.2 g (22.7 mL, 83.6 mmol) of tri-n-butyltin chloride (STREM Chemicals, 96%), which was then added dropwise to the reaction mixture over a period of 0.5 h. The mixture was let to warm slowly to room temperature over a period of 12 h, then 400 mL of sat. $NaHCO_3$ was added and extracted with dichloromethane (2×200 mL). The dichloromethane extract was dried over $Na_2SO_4$ (10 g) and the solvent was removed by rotary evaporation under reduced pressure (14 mm) at 40° C. The remaining brownish oil was dried under vacuum (0.1 mm) over a period of 12 h to give 38.7 g of crude material which has good purity by $^1H$ NMR and was used for the next step. $^1H$ NMR (300 MHz, $CDCl_3$): δ7.61 (dd, $J_1$=7.3 Hz, J2=8.1 Hz, 1H, H4), 7.38 (d, J=7.3 Hz, 1H, H3), 7.01 (d, J=8.1 Hz, 1H, H5), 5.90 (s, 2H, H8), 2.14 (s, 6H, H11), 1.55 (t, J=7.6 Hz, 6H, H13), 1.32 (m, 6H, H14), 1.11 (m, 6H, H15), 0.86 (t, J=7.3 Hz, 9H, H16) $^{13}C$ NMR (76 MHz, $CDCl_3$): δ174.0, 151.9, 134.5, 130.5, 128.4 (=2C), 119.8, 106.3 (=2C), 29.0 (=3C), 27.2 (=3C), 13.6 (=3C), 13.2 (=2C), 9.9 (=3C). EI-MS (70 eV, quadrupole), m/z (rel. intensity): 462 (M+, 5), 460 (4), 405 (25), 403 (19), 349 (17), 347 (17), 291 (100), 171 (69), 144 (16).

E. Synthesis of Intermediate 22—(6,7-Dihydro-2-(2-(2,5-dimethyl-1H-pyrrol-1-yl)pyridin-6-yl)-8 (5H)-quinolinone)

A 250-mL round-bottomed flask equipped with a stirring bar, condenser and nitrogen gas inlet was charged with 2.00 g (11.01 mmol) of 2-chloro-6,7-dihydro-8(5H)-quinolinone (19), 7.62 g (16.52 mmol) of 2-tri-n-butylstannyl-6-(2,5-dimethyl-1H-pyrrol-1-yl)pyridine (21), 0.77 g (1.1 mmol) of bis(triphenylphosphine)palladium (II) dichloride (STREM Chemicals) and 300 mL of anhydrous toluene. The mixture was heated under reflux, under nitrogen for 25 h. Then the mixture was cooled to room temperature and the solvent was evaporated to dryness. The resulting residue was dissolved in 10 mL chloroform and passed through the column (silica gel, 500 mL of $CHCl_3$). The composition of fractions were checked by GCMS. The first light-yellow fraction did not contain the product by GCMS and was discarded. The front of the second fraction was moving on silica gel as a reddish band. Starting from the second fraction, everything was collected as a one fraction. The purified solution was evaporated to dryness. Then 1.0 mL of ethyl acetate was added and the mixture was swirled to form a suspension, then 70 mL of hexane was added and swirled. The mixture was cooled in a freezer over a period of 12 h. The precipitate was collected by vacuum filtration, washed with 5 mL of cold hexane and dried under vacuum (0.1 mm) to give 2.06 g (59%) of 22. $^1H$ NMR (300 MHz, $CDCl_3$): δ8.61 (d, J=7.69 Hz, 1H, H9), 8.53 (d, J=8.06 Hz, 1H, H3), 7.96 (dd, J1=J2=7.69 Hz 1H, H10), 7.77 (d, J=8.06 Hz, 1H, H4), 7.25 (d, J=7.69 Hz, 1H, H11), 5.95 (s, 2H, H12), 3.09 (t, J=6.23 Hz, 2H, H7), 2.86 (t, J=6.23 Hz, 2H, H5), 2.24 (m, 2H, H6), 2.20 (s, 6H, $CH_3$); $^{13}C\ NMR$ (76 MHz, $CDCl_3$): δ196.4, 155.1, 154.8, 151.2, 147.6, 141.2, 138.9, 138.6, 128.6 (=2C), 124.6, 121.9, 120.0, 107.1 (=2C), 40.0, 29.3, 22.8, 13.2 (=2C). For microanalysis a sample was recrystallized from ethyl acetate and dried under vacuum (0.1 mm, RT) for 24 h, mp 183–185° C. Anal. Calcd. for $C_{20}H_{19}N_3O$: C, 75.69; H, 6.03; N, 13.24%. Found: C, 75.30; H, 5.69; N, 13.25%.

F. Synthesis of Intermediate 23—(5,6,9,10-Tetrahydro-13-(2-(2,5-dimethyl-1H-pyrrol-1-yl) pyridin-6-yl)[1,10]phenanthrolino[2,3-b][1,10] phenanthroline-2-carboxylic acid, potassium salt).

A 50-mL round-bottomed flask equipped with a stirring bar, condenser and nitrogen gas inlet was charged with 0.310 g (1.15 mmol) of 5,6-dihydro-9-amino-8-[1,10] phenanthrolinecarboxaldehyde-2-carboxylic acid (13) and 15 mL of methanol. The mixture was stirred and heated to boiling under nitrogen. Then 25 mL of toluene was added and KOH solution in methanol was introduced dropwise to achieve pH 9 (approximately 30 drops of 1.055 N KOH solution was required). A thick gel formed which was swirled manually three times with 1 min intervals. Then a suspension of 0.365 g (1.15 mmol) of 6,7-dihydro-2-(2-(2, 5-dimethyl-1H-pyrrol-1-yl)pyridin-6-yl)-8(5H)-quinolinone (22) in 2 mL of methanol was added and the mixture was heated under reflux, under nitrogen for 3 days. Then the solvent was completely removed by rotary evaporation. The resulting residue was taken into 10 mL of methanol, then 80 mL of ether was added and the mixture was cooled in a freezer for a period of 12 h. The precipitate was collected by vacuum filtration, washed with 5 mL of ice cold ether and dried under vacuum (0.1 mm) to give 0.454 g (67%) of potassium salt 23; dec.>380° C. $^1H$ NMR (300 MHz, DMSO-$d_6$): δ8.70 (br., 1H, H3), 8.31 (d, J=8.1 Hz, 1H, H12), 8.28 (s, 1H, H7), 8.22 (s, 1H, H8), 8.03 (m, 3H, H4,11,16), 7.73 (d, J=8.1 Hz, 1H, H15), 7.50 (d, J=8.1 Hz, 1H, H17), 5.93 (s, 2H, H18), 3.22 (s, 2H, H5), 3.18 (s, 2H, H6), 3.08 (s, 4H, H9,10), 2.25 (s, 6H, $CH_3$). FAB-MS, m/z (rel. intensity): 627.3 (M+39 (K+), 38), 589.3 (M+1, 75), 545.3 (M−44+1, 100).

G. Synthesis of Compound IC—(5,6,9,10-Tetrahydro-13-(2-aminopyridin-6-yl)[1,10] phenanthrolino[2,3-b][1,10]phenanthroline-2-carboxylic acid)

A 50-mL round-bottomed flask equipped with a stirring bar, condenser and nitrogen gas inlet was charged with 0.320 g (0.544 mmol) of 5,6,9,10-tetrahydro-13-(2-(2,5-dimethyl-1H-pyrrol-1-yl)pyridin-6-yl)[1,10]phenanthrolino[2,3-b][1, 10] phenanthroline-2-carboxylic acid potassium salt (23), 0.7 g (10 mmol) of hydroxylamine hydrochloride (ACROS, 97%), 6 mL of water and 16 mL of ethanol. The mixture was stirred and heated under reflux, under nitrogen over a period of 3 days and then cooled in a refrigerator over a period of 12 h. The precipitate was collected by vacuum filtration, washed with water (2×5 mL) and dried under vacuum (0.1 mm) to give 0.168 g (65%) of 8 (compound IC); mp 275–280° C. with dec. $^1H$ NMR (300 MHz, TFA-$d_1$): δ11.03 (s, 1H, H7), 10.84 (d, J=8.1 Hz, 1H, H3), 10.74 (d, J=8.1 Hz, 1H, H4), 10.72 (s, 1H, H8), 10.33 (d, J=8.1 Hz, 1H, H12), 10.14 (d, J=8.1 Hz, 1H, H11), 10.00 (dd, J1=8.1 Hz, J2=7.7 Hz, 1H, H16), 9.60 (d, J=7.3 Hz, 1H, H15), 9.15 (d, J=8.8 Hz, 1H, H17), 5.55–5.42 (m, 4H, H5,6,9,10); $^{13}C$ NMR (125.7 MHz, TFA-$d_1$): δ162.2, 157.3, 153.0, 151.6, 150.2, 150.1, 148.3, 147.3, 147.0, 146.7, 145.3, 144.8, 144.0, 142.9, 142.7, 141.2, 141.0, 139.5, 139.2, 131.6, 128.7 (=2C), 117.6, 113.4, 27.7, 27.3, 27.2, 26.8. IR (KBr): v3422(br. s), 2940(w), 1735(m), 1663(s), 1617(s), 1571(w), 1541(m), 1508(w), 1467(m), 1437(m), 1399(w), 1360(m), 1284(w), 1247(w), 1213(m), 1173(w), 1067(w), 931(w), 809(m), 774 (w), 737(w), 710(w), 621(w), 585(w), 478(w). FAB-MS, m/z (rel. intensity): 473.4 (M+1, 100), 429.4 (M−44+1, 100).

Example 4

Synthesis of Compound ID—(5,6,9,10-Tetrahydro-13-(4,6-dihydroxypyrimidin-2-yl)[1,10] phenanthrolino[2,3-b][1,10]phenanthroline-2-carboxylic acid, potassium salt)

Figure 4:
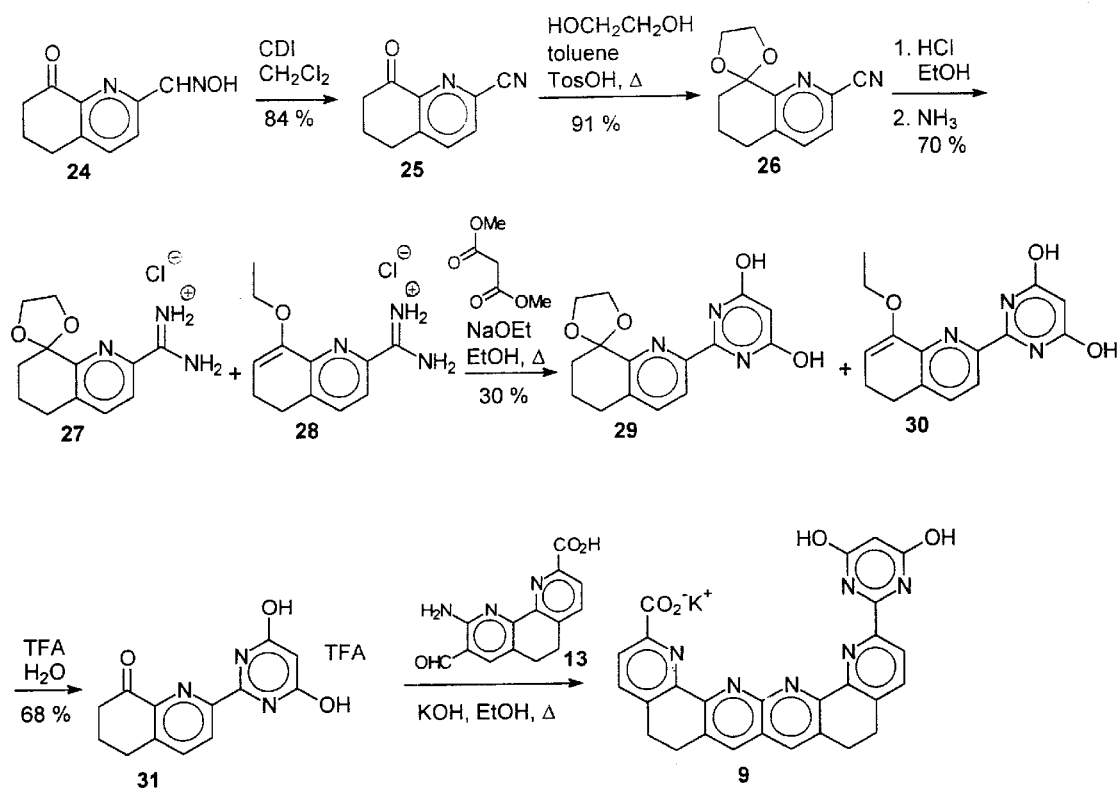
FIG. 4 is a reaction scheme illustrating the synthesis of compound ID of the present invention.

4,6-Dihydroxypyrimidines can be made by condensation of dimethylmalonate with amidines (Davoll et al., *J. Chem. Soc.* 1956, 2124–2131). For amidine synthesis Pinner's method (Pinner, *Ber.* 1883, 16, 1654; Pinner, *Ber.* 1884, 17, 178) was chosen. First, aldoxime 24 was dehydrated to nitrile 25 with 1,1-carbonyldiimidazole (CDI) according to known methodology (Foley et al., *J Chem. Soc., Chem. Commun.* 1973, 628–629). The ketone group in 25 was protected with ethylene glycol in toluene with a catalytic amount of p-toluenesulfonic acid to give dioxolane 26. Using Pinner's conditions, the cyano group in 26 was transformed to the amidinium, which gave a mixture of amidines 27 and 28. The first step involves acid catalyzed conversion of the cyano group of 26 to an imidate. ether. At this stage the dioxolane ring is cleaved and partially transformed to the ethyl vinyl ether group of 28. Since dioxolanes and vinyl ethers are stable under basic conditions, we carried this mixture through the next step without separation. Condensation with dimethylmalonate in an ethanolic solution of NaOEt gave the corresponding mixture of dihydroxypyrimidines 29 and 30, which were purified from other byproducts by column chromatography. Hydrolysis of the dioxolane ring and the ethyl vinyl ether group was accomplished at room temperature in a TFA/water mixture. The starting mixture of 29 and 30 goes into solution and product 31 precipitates from solution as a salt of trifluoroacetic acid. Condensation of ketone 31 with aminoaldehyde 13 under basic conditions in ethanol provides the final receptor as potassium salt 9 compound ID. A reaction scheme illustrating the synthesis of compound ID is shown in FIG. 4. The synthesized compounds were analyzed by 1H and $^{13}$C NMR, and Mass Spectrometry as in Example 1.

A. Synthesis of Intermediate 25—(2-Cyano-6,7-dihydro-8(5H)-quinolinone)

A 250-mL round-bottomed flask equipped with a condenser, nitrogen gas inlet and magnetic stirring bar was charged with 11.9 g (62.6 mmol) of 6,7-dihydro-8(5H)-quinolinone-2-carbaldoxime (24) and 80 mL of dichloromethane. The mixture was stirred and to the resulting suspension 11.4 g (68.8 mmol) of 1,1'-carbonyldiimidazole was added. The mixture was heated under reflux under nitrogen over a period of 6 h. Then, the solvent was removed by rotary evaporation and the resulting residue was dissolved in 40 mL of hot ethanol. The ethanol solution was cooled in a freezer for a period of 12 h and the resulting precipitate was collected by vacuum filtration, washed with ice cold ethanol (2×5 mL) and dried under vacuum (0.1 mm) to give 9.1 g (84%) of nitrile 25; mp145–148 ° C. $^1$H NMR (300 MHz, CDCl$_3$): δ7.85 (d, J=8.1 Hz, 1H, H3), 7.75 (d, J=8.1 Hz, 1H, H4), 3.13 (t, J=6.0 Hz, 2H, H7), 2.87 (t, J=6.6 Hz, 2H, H5), 2.25 (m, 2H, H6); $^{13}$C NMR (76 MHz, CDCl$_3$): δ194.3, 149.0, 144.0, 139.1, 132.7, 130.6, 116.3, 39.3, 29.1, 21.8. EI-MS (70 eV, quadrupole), m/z (rel. intensity): 172 (M+,68), 143 (41), (41), 116 (67), 89 (18), 76 (6), 63 (12), 55 (100). For microanalysis a sample was dried under vacuum (0.1 mm) at 60° C. for 3 days. Anal. Calcd for C10H8N2: OC, 69.76; H, 4.68; N, 16.26% Found: C, 69.45; H, 4.37; N, 16.34%.

B. Synthesis of Intermediate 26—(Spiro[1,3-dioxolane-2,8(7H)-(2-cyano-5,6-dihydroquinoline)])

A 500-mL round-bottomed flask equipped with a Dean-Stark adapter, condenser, nitrogen gas inlet and a magnetic stirring bar was charged with 8.65 g (50.2 mmol) of 2-cyano-6,7-dihydro-8(5H)-quinolinone (25), 3.37 g (54.3 mmol) of ethylene glycol, 200 mL of toluene and 0.5 g of p-toluenesulfonic acid. The mixture was heated under reflux under nitrogen over a period of 16 h. Then 200 mL of toluene was added and the mixture was washed with 200 mL of sat. NaHCO$_3$, then with 100 mL of sat. NaCl. The toluene solution was dried over Na$_2$SO$_4$ (4 g), and the solvent was removed by rotary evaporation. The resulting residue was dissolved in 40 mL of hot ethanol, and the ethanol solution was cooled in a freezer for a period of 12 h. The resulting precipitate was collected by vacuum filtration, washed with ice cold ethanol (2×5 mL) and dried under vacuum (0.1 mm) to give 9.83 g (91%) of dioxolane 26; mp 110–114 ° C. $^1$H NMR (300 MHz, CDCl$_3$); δ7.55 (d, J=8.1 Hz, 1H, H3), 7.51 (d, J=8.1 Hz, 1H, H4), 4.49 (t, J=6.4 Hz, 2H, H9b), 4.15 (t, J=6.9 Hz, 2H, H9a), 2.87 (t, J=6.2 Hz, 2H, H5), 2.13 (t, J=5.5 Hz, 2H, H7),, 2.03 (m, 2H, H6); $^{13}$C NMR (300 MHz, CDCl$_3$): δ158.7, 137.4, 137.1, 131.0, 127.1, 117.3, 105.0, 66.0 (=2C), 34.8, 28.7, 20.0. EI-MS (70 eV, quadrupole), m/z (rel. intensity): 215 (M−1,2), 173 (100), 155 (8), 144 (8), 99 (26), 55 (17). A sample (100 mg) was recrystallized from MeOH (3 mL) and dried under vacuum (0.1 mm, RT, 2 days) to give 78 mg of 26; mp 112–114° C. Anal. Calcd for C$_{12}$H$_{12}$N$_2$O$_2$: C, 66.66; H, 5.59; N, 12.95%. Found: C, 66.71; H, 5.58; N, 13.11%.

C. Synthesis of Intermediates 27 (Spiro[1,3-dioxolane-2,8(7H)-(5,6-dihydroquinoline-2-carbamidine)]) and 28 (5,6-Dihydro-8-ethoxyquinoline-2-carbamidine)

A 250-mL round-bottomed two-necked flask equipped with calcium chloride drying tube in one neck, glass tube with rubber adaptor in another neck and magnetic stirring bar was charged with 10.0 g (46.25 mmol) of spiro[1,3-dioxolane-2,8(7H)-(2-cyano-5,6-dihydroquinoline)] (26) and 10 mL of absolute ethanol. The flask was immersed into ice bath and the mixture was vigorously stirred. Then a flow of dry HCl gas (Aldrich, 99.9%) was bubbled through the reaction mixture via glass tube over a period of 1 h. By this time all solid material went into solution. Then the glass tube with rubber adaptor was replaced by septum and the reaction mixture was stirred at room temperature over a period of 12 h. By this time a thick yellow paste of ethyl imidate formed. Then the flask was immersed into ice bath, calcium chloride tube was removed and 150 mL of ice cold saturated solution of ammonia in absolute ethanol was carefully added into the mixture. The opened neck was closed with a septum and both septa were secured by copper wire. The mixture was stirred at room temperature over a period of 4 days. Then the precipitated ammonium chloride was removed by vacuum filtration, the remaining clear solution was evaporated to dryness and the resulting solid residue was continuously extracted in a soxhlet with 300 mL of ethyl acetate over a period of 3 days. While being hot, the extract was filtered through Whatman # 2 filter paper, concentrated to 60 mL by boiling off the solvent and cooled slowly first to room temperature (5 h), then in a freezer over a period of 12 h. The precipitate was collected by vacuum filtration, washed with 10 mL of cold ethyl acetate and dried under vacuum (0.1 mm) to give 6.74 g of the first crop. The mother liquor was concentrated to 7 mL to give additional precipitate which was collected as above to give 1.87 g of the second crop. The combined crops yielded 8.61 g of the mixture of 27 and 28 (approximately 70%). Both crops consisted of a fine white powder of dioxolane adduct (27) and larger brown crystals of ethoxyvinyl ether adduct (28), which could be separated mechanically by removing big crystals from the powder. However, the mixture of 27 and 28 can be used directly in the next step.

Intermediate 27: mp 165–168° C. $^1$H NMR (300 MHz, DMSO-d$_6$): δ7.85 (d, J=7.69 Hz, 1H, H3), 7.68 (d, J=7.69 Hz, 1H, H4), 7.65 (s, 2H, NH), 7.59 (s, 2H, NH), 4.37 (s, 2H, H9b), 4.00 (s, 2H, H9a), 2.79 (t, J=5.5 Hz, 2H, H5), 1.95 (m, 2H, H7), 1.85 (m, 2H, H6); $^{13}$C NMR (125.7 MHz, DMSO-d$_6$): δ165.8, 155.4, 147.9, 138.3, 135.8, 121.1, 105.2, 65.7, 35.1, 28.0, 20.2. FAB-MS, m/z (rel. intensity): 235.3 (M+1, 100), 219.3 (28).

Intermediate 28: mp 135–137° C. $^1$H NMR (300 MHz, DMSO-d$_6$): δ7.79 (d, J=7.69 Hz, 1H, H3), 7.69 (d, J=7.69 Hz, 1H, H4), 7.64 (s br., 4H, NH), 5.40 (dd, J1=4.40 Hz, J2=4.76 Hz, 1H, H7), 3.85 (q, J=6.96 Hz, 2H, Et (CH$_2$)), 2.79 (t, J=7.87 Hz, 2H, H5), 2.30 (m, 2H, H6), 1.32 (t, J=6.96 Hz, 3H, CH$_3$); $^{13}$C NMR (75.5 MHz, DMSO-d$_6$): δ166.2, 150.9, 148.5, 147.6, 136.1, 135.9, 120.6, 103.2, 62.9, 27.3, 21.0, 14.7. IR (KBr): ν3434(m), 3446((w), 3189(br. m), 2979(w), 2927(w), 2894(w), 2838(w), 1696(s), 1629(m), 1577(m), 1450(w), 1431(m), 1387(m), 1354(w), 1319(w), 1276(m), 1259(m), 1224(w), 1171(m), 1139(w), 1115(w), 1097(m), 1066(m), 1022(w), 922(w), 856(m), 783 (m), 740(w), 665(w), 607(w), 512(m). 2FAB-MS, m/z (rel. intensity): 219 (M+2, 100), 174 (18).

D. Synthesis of Intermediates 29 (Spiro[1,3-dioxolane-2,8(7H)-(5,6-dihydro-2-(4,6-dihydroxy-2-pyrimido)quinoline)]) and 30 (5,6-Dihydro-2-(4,6-dihydroxy-2-pyrimido)-8-ethoxyquinoline)

A 250 mL single-necked, round-bottomed flask equipped with a condenser fitted with a nitrogen gas inlet and a magnetic stirring bar was charged with 5.55 g (20 mmol) of mixture of spiro[1,3-dioxolane-2,8(7H)-(5,6-dihydroquinoline-2-carbamidine)] (27) and 5,6-dihydro-8-ethoxyquinoline-2-carbamidine (28) and 2.99 g of dimethylmalonate (ACROS, 99%). The flask was flushed with nitrogen, then 100 mL of 3 M solution of sodium ethoxide in anhydrous ethanol was added and the mixture was heated at 90° C. under nitrogen over a period of 36 h. After dilution of the mixture with 70 mL of ethanol, it was cooled by means of an ice bath and conc. HCl was added slowly until pH 5 was reached. The precipitated NaCl was filtered off and washed with ethanol (5×20 mL). The ethanolic solution was evaporated and the resulting residue was purified by column chromatography (silica gel) eluting first with CHCl$_3$/MeOH (95/5) mixture to give unidentified by products, and then with CHCl$_3$/MeOH (90/10) to give 1.80 g (~30%) mixture of 29 and 30 as an oil which solidified upon standing at room temperature over 12 h.

Intermediate 30: $^1$H NMR (300 MHz, DMSO-d$_6$): δ11.6 (s br., 1H, OH), 10.8 (s br., 1H, OH), 8.00 (d, J=7.69 Hz, 1H, H3), 7.80 (d, J=7.69 Hz, 1H, H4), 5.47 (dd, J1=4.39 Hz, J2=5.13 Hz, 1H, H7), 5.37 (s, 1H, H9), 3.89 (q, J=6.83 Hz, 2H, Et (CH$_2$)), 2.85 (t, J=7.69 Hz, 2H, H5), 2.33 (m, 2H, H6), 1.34 (s, 3H, CH$_3$); FAB-MS, m/z (rel. intensity): 286 (M+1, 100), 176 (38).

E. Synthesis of Intermediate 31—(6,7-Dihydro-2-(4,6-dihydroxypyrimidin-2-yl)-8(5H)-quinolinone trifluoroacetate)

A 50-mL round-bottomed flask equipped with a magnetic stirring bar was charged with 1.43 g (~4.7 mmol) of mixture of spiro[1,3-dioxolane-2,8(7H)-(5,6-dihydro-2-(4,6-dihydroxy-2-pyrimido)quinoline)] (29) and 5,6-dihydro-2-(4,6-dihydroxy-2-pyrimido)-8-ethoxyquinoline (30), 9 mL of water and 12 mL of trifluoroacetic acid. The mixture was stirred at room temperature over a period of 24 h. A precipitate formed by this time, which was collected by vacuum filtration, washed with 5 mL of ice cold water and dried under vacuum (0.1 mm, RT) over a period of 24 h. to give 1.18 g (68%) of TFA salt 31; dec.>350° C. $^1$H NMR (300 MHz, DMSO-d$_6$): δ8.25 (d, J=8.06 Hz, 1H, H3), 8.07 (d, J=8.05 Hz, 1H, H4), 5.40 (s, 1H, H9), 4.0 (br., OH), 3.07 (t, J=5.50 Hz, 2H, H7), 2.75 (t, J=6.23 Hz, 2H, H5), 2.09 (J1=5.12 Hz, J2=6.23 Hz, 2H, H6); $^{13}$C NMR (125.7 MHz, DMSO-d6): δ195.4, 166.7, 154.4, 147.1, 146.8, 144.6, 140.2, 125.1, 90.6, 39.6, 28.7, 22.1. FAB-MS, m/z (rel. intensity): 258.3 (M+1, 100). Anal. Calcd for C$_{15}$H$_{12}$F$_3$N$_3$O$_5$: C, 48.51; H, 3.26; N, 11.32%. Found: C, 48.88; H 3.05; N, 12.64%.

F. Synthesis of Compound ID—(5,6,9,10-Tetrahydro-13-(4,6-dihydroxypyrimidin-2-yl) [1,10]phenanthrolino [2,3-b][1,10]phenanthroline-2-carboxylic acid, potassium salt).

A 50-mL round-bottomed flask equipped with a stirring bar, condenser and nitrogen gas inlet was charged with 86 mg (0.32 mmol) of 5,6-dihydro-9-amino-8-[1,10] phenanthrolinecarboxaldehyde-2-carboxylic acid (13), 119 mg (0.32 mmol) of 6,7-dihydro-2-(4,6-dihydroxypyrimidin-2-yl)-8(5H)-quinolinone trifluoroacetate (31) and 25 mL of ethanol. The mixture was heated to boiling and then KOH solution in methanol was added dropwise to achieve pH 9 (approximately 30 drops of 1.055 N KOH solution was required). The resulting mixture was heated under reflux, under nitrogen for 48 h. Then the solvent was partially evaporated to 10 mL, 20 mL of ether was added and the mixture was cooled in a freezer for a period of 12 h. The precipitate was collected by vacuum filtration, washed with 5 mL of ice cold ether and dried under vacuum (0.1 mm) to give 198 mg of potassium salt 9 (compound ID). $^1$H NMR (300 MHz, D$_2$O): δ7.64 (d, J=7.7 Hz, 1H, H3), 7.37 (d, J=7.7 Hz, 1H12), 7.32 (d, J=7.7 Hz, 1H, H4), 7.10 (d, J=7.7 Hz, 1H, H11), 6.80 (s, 1H, H7), 6.76 (s, 1H, H8), 6.58 (s, 1H, H15), 3.63 (s, 4H, H9,10), 3.32 (br., 2H, H5), 2.62 (br., 2H, H6). $^{13}$C NMR (125.7 MHz, TFA-d$_1$): δ171.8, 161.8, 156.1, 152.7, 152.0, 150.4, 149.0, 148.9, 148.7, 147.4, 146.8, 146.7, 144.7, 143.8, 143.0, 141.5, 140.9, 139.8, 139.1, 131.6, 131.0, 128.9, 27.4, 27.1, 26.8. IR (KBr): ν3385(br. s), 1624(s), 1578(s), 1559(s), 1477(m), 1442(m), 1377(s), 1315 (m), 1292(m), 1204(w), 1159(w), 1099(w), 1074(m), 1027 (w), 978(w), 927(w), 872(w), 808(m), 782(w), 763(w), 735(w), 707(w), 625(w), 590(w), 519(w). FAB-MS, m/z (rel. intensity): 529.3 (M+1, 100), 498.3 (28), 485.3 (32). For microanalysis 50 mg of crude 9 (compound ID) was dissolved in 3 mL of water at boiling, then 7 mL of EtOH was added and cooled to RT. The precipitate was collected by vacuum filtration, washed with 2 mL of EtOH and dried under vacuum (0.1 mm, RT) for 4 days, dec.>380° C. Anal. Calcd for C$_{27}$H$_{17}$KN$_6$O$_4$: C, 59.32; H, 3.50 ; N, 15.38% Found: C, 59.01; H, 3.83; N, 15.11%.

Example 5

Synthesis of Compound IE—(5,6,9,10-Tetrahydro [1,10]phenanthrolino[2,3-b][1,10]phenanthroline-2-(N-(4-aminoethyl-N'-(4-tert-butoxycarbonyltoluidyl) naphthyridine))carboxamide-13-(N-(2,5-dimethoxy-4-dimethylaminophenethyl))carboxamide)

Figure 5:
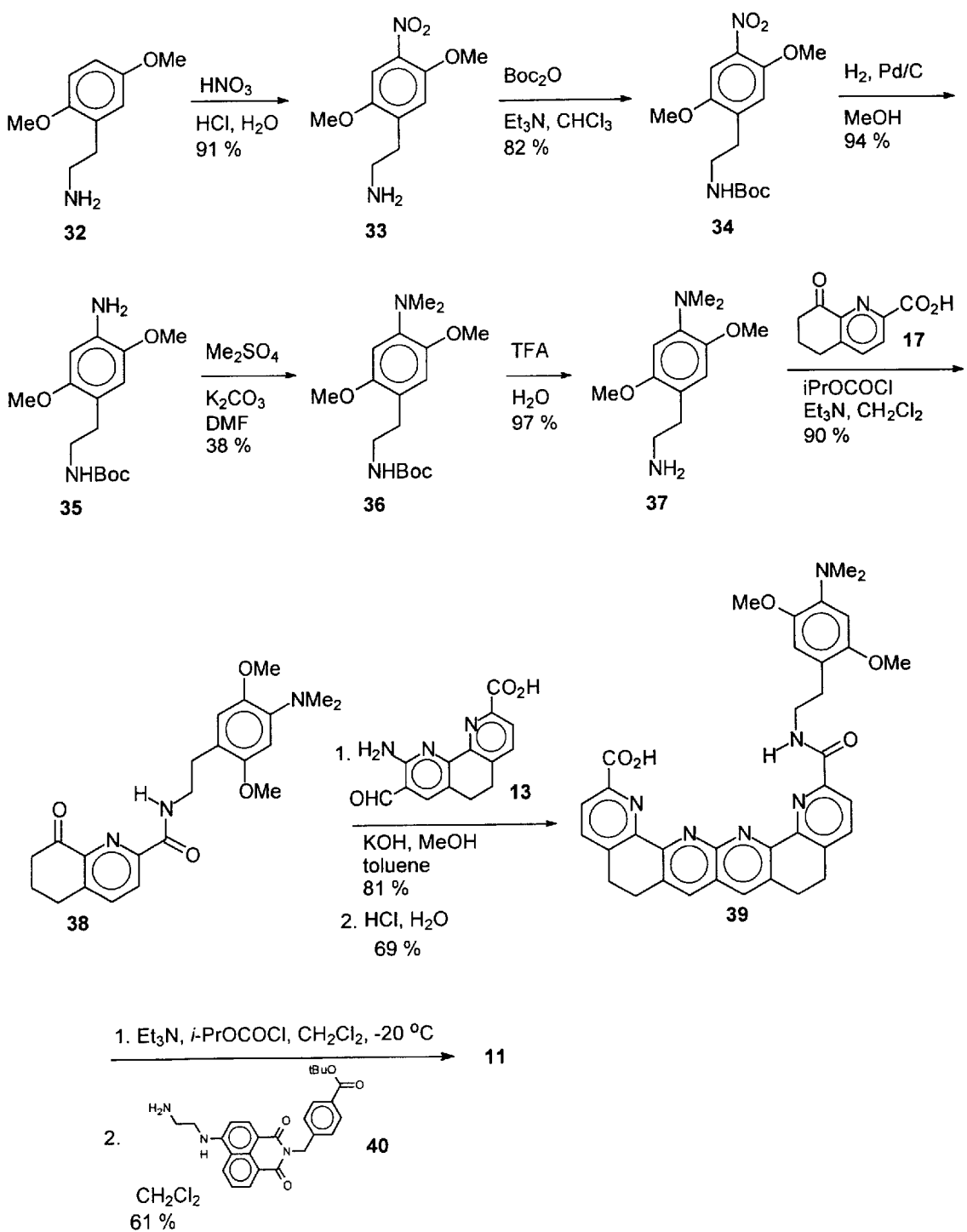
FIG. 5 is a reaction scheme illustrating the synthesis of compound IE of the present invention.

For the synthesis of quencher, dimethoxyphenylethylamine 32 was nitrated in HNO$_3$/aq.HCl mixture. Because the reaction is exothermic, it is important to add $HNO_3$ slowly, so the temperature does not rise above 10° C. After work up, the isolated oil solidified to give 33 in good yield and purity. The amino group in 33 was protected with $Boc_2O$ in chloroform. After work up, a crude oil of 34 was crystallized in EtOAc/hexane mixture. Catalytic reduction of the nitro group in 34 was achieved by atmospheric hydrogenation on Pd/C catalyst in methanol at room temperature. The reaction is very clean and simple removal of the catalyst followed by evaporation and drying yields 35 in a good yield and high purity. Alkylation of the free amino group in 35 with an excess of dimethyl sulfate, followed by column chromatography provided desired dimethylated product 36 in 38% yield. Deprotection of 36 was accomplished by brief exposure to a TFA/water mixture at room temperature, which yielded free amine 37. In the next step, ketoacid 17 (Bell et al., *Angew. Chem., Int. Ed. Engl.*, 1999, 38, 2543–2547) was first activated with isopropyl chloroformate in dichloromethane at −20° C. under nitrogen. Then amine 37 was slowly introduced to the activated carboxylate, leading to clean formation of amide 38. Friedländer condensation of ketoamide 38 with aminoaldehyde 13 (Bell et al., *Angew. Chem., Int. Ed. Engl.*, 1999, 38, 2543–2547) was done in MeOH/toluene mixture to give potassium salt of 39, which was then acidified in water with HCl to give neutral acid form of 39. Then, acid 39 was activated with isopropylchloroformate in dichloromethane and treated with amine fluorophore 40 at −20° C. After column chromatography, crude receptor 11 was further purified by recrystallization from ethyl acetate with a small amount of $CH_2Cl_2$, which provided 11 in analytically pure form. A reaction scheme for compound IE is shown in FIG. 5.

A. Synthesis of Intermediate 33—(2,5-Dimethoxy-4-nitrophenethylamine)

To a 100-mL Erlenmeyer flask equipped with a magnetic stirring bar were added 4.73 g (26.1 mmol) of 2,5-dimethoxyphenethylamine (32) (Trans World Chemicals Inc., 98%) and 4.2 mL of water. The mixture was stirred and cooled to 0° C. in an ice bath and 3.1 mL of conc. HCl was added slowly. To the resulting yellow solution 3.4 mL of conc. $HNO_3$ was added dropwise at 0–5° C. over a period of 1 h. Then 12 mL of water was added to the solidified mixture and swirled to form a stirrable paste. Then another 3.4 mL of conc. $HNO_3$ was added dropwise at 0–5° C. over a period of 1 h. The yellow mixture was refrigerated for 12 h., then 20 mL of water was added and ultrasonicated to brake big chunks of solid. The suspension was cooled to 0° C. in an ice bath and 10 mL of 40% NaOH was added slowly to achieve pH 12–13. The mixture was extracted with $CHCl_3$ (3×10 mL) and the combined extract was washed with 0.5 N NaOH (3×10 mL), dried over $K_2CO_3$ (3 g) and evaporated to dryness (15 mm) to give 5.4 g (91%) of 33 as a brown oil which solidified after 0.5 h at room temperature. $^1H$ NMR (300 MHz, $CDCl_3$): δ7.43 (s, 1H, H3), 6.96 (s, 1H, H6), 3.95 (s, 3H, H10), 3.85 (s, 3H, H9), 3.00 (t, J=6.9 Hz, 2H, H8), 2.85 (t, J=6.9 Hz, 2H, H7), 2.06 (s, 2H, $NH_2$); $^{13}C$ NMR (75.7 MHz, $CDCl_3$): δ150.6, 147.3, 136.8, 136.5, 116.2, 107.2, 56.9, 55.8, 41.6, 34.9. FAB-MS, m/z (rel. intensity): 227.3 (M+1, 100). For microanalysis crude 33 was recrystallized from a 1:5 mixture of EtOAc/hexane and dried under vacuum (0.1 mm, RT) for 2 days; mp 64–66° C. Anal. Calcd for $C_{10}H_{14}N_2O_4$: C, 53.09; H, 6.23; N, 12.38%. Found: C, 53.04; H, 6.03; N, 12.30%.

B. Synthesis of Intermediate 34—(N-t-butoxycarbonyl-2,5-dimethoxy-4-nitrophenethylamine)

A 100-mL round-bottomed flask equipped with a stirring bar, condenser and nitrogen gas inlet was charged with 5.4 g (23.9 mmol) 2,5-dimethoxy-4-nitrophenethylamine (33), 3.6 g (35.6 mmol) triethylamine and 30 mL of $CHCl_3$. Then a solution of 6.3 g (28.6 mmol) of di-t-butyl dicarbonate (Aldrich, 97%) in 6 mL of $CHCl_3$ was added slowly at room temperature. The mixture started to boil, then the reaction ceased. After stirring for 25 min. at room temperature, the mixture was washed with 0.4 N HCl (3×50 mL), then with water (50 mL) and dried over $Na_2SO_4$ (3 g). The solvent was removed under reduced pressure (14 mm) to give 9.4 g of brown oil. The crude oil was dissolved in 5 mL of EtOAc and 50 mL of hexane was added. The solution was cooled in a freezer and crystallization was induced by scratching with a glass rod. The precipitate was rapidly collected by vacuum filtration while cold, washed with 25 mL of ice cold hexane and dried under vacuum (0.1 mm, RT) for 24 h to give 6.4 g (82%) of yellow solid of 34; mp 66–68° C. $^1H$ NMR (300 MHz, $CDCl_3$): δ7.42 (s, 1H, H3), 6.92 (s, 1H, H6), 3.94 (s, 3H, H10), 3.85 (s, 3H, H9), 4.6 (br s, 1H, NH), 3.37 (t, J=6.4 Hz, 2H, H8), 2.87 (t, J=6.8 Hz, 2H, H7), 1.44 (s, 9H, $C(CH_3)_3$); $^{13}C$ NMR (75.5 MHz, $CDCl_3$): δ155.6, 150.6, 147.3, 137.2, 135.3, 116.3, 107.3, 79.1, 57.0, 55.9, 39.7, 31.1, 28.2. FAB-MS, m/z (rel. intensity): 326.4 (48), 271.3 (100), 270.3 (68), 227.3 (48). Anal. Calcd for $C_{15}H_{22}N_2O_6$: C, 55.20; H, 6.79; N, 8.58%. Found: C, 55.03; H, 6.95; N, 8.32%.

C. Synthesis of Intermediate 35—(N-t-Butoxycarbonyl-4-amino-2,5-dimethoxyethylamine).

A 250-mL Morton flask equipped with a stirring bar was charged with 5.77 g (17.7 mmol) N-t-butoxycarbonyl-2,5-dimethoxy-4-nitrophenethylamine (34), 65 mL of methanol and 0.6 g of palladium on activated carbon (ACROS, 10% Pd). The flask was attached to a low-pressure hydrogenation apparatus. The entire system was evacuated at water aspirator pressure (20–30 mm) and filled with hydrogen gas. The evacuation/filling procedure was repeated three more times. The contents were stirred vigorously at room temperature over a period of 4 h, when 1.3 L (47.6 mol) of hydrogen was consumed and the reaction stopped. The precipitated solid was redissolved by addition of 30 mL of methanol and heating to 50° C. Then the catalyst was removed by vacuum filtration through Whatman No. 2 filter paper and washed with 10 mL of methanol. The solvent was evaporated under reduced pressure (14 mm) and the white residue was dried under vacuum (0.1 mm) for a period of 24 h to give 4.94 g (94 %/) of 35. $^1H$ NMR (300 MHz, $CDCl_3$): δ6.59 (s, 1H, H6), 6.33 (s, 1H, H3), 4.6 (br s, 1H, NH), 3.80 (s, 3H, H9), 3.74 (s, 3H, H10), 3.28 (t, J=6.6Hz, 2H, H8), 2.70 (t, J=6.9 Hz, 2H, 7), 1.43 (s, 9H, $C(CH_3)_3$); $^{13}C$ NMR (75.5 MHz, $CDCl_3$): δ155.8, 151.8, 140.9, 134.9, 116.2, 113.7, 99.6, 78.6, 56.1, 55.7, 41.0, 30.0, 28.3. FAB-MS, m/z (rel. intensity): 296.4 (100), 241.3 (35). For microanalysis crude 35 was recrystallized from MeOH and dried under vacuum (0.1 mm, RT) for2 days, mp 117–119° C. Anal. Calcd for $C_{15}H_{24}N_2O_4$: C, 60.79; H, 8.16; N, 9.45%. Found: C, 60.91; H, 7.90; N, 9.49%.

D. Synthesis of Intermediate 36—(N-t-Butoxycarbonyl-2,5-dimethoxy-4-dimethylaminophenethylamine)

A 50-mL 3-neck round-bottomed flask equipped with a stirring bar, condenser, thermometer and nitrogen gas inlet was charged with 4.84 g (16.3 mmol) of N-t-butoxycarbonyl-4-amino-2,5-dimethoxyethylamine (34) and 3.84 g (27.8 mmol) of anhydrous $K_2CO_3$. The flask was closed with a septum and 9 mL of anhydrous DMF was added via syringe. The mixture was stirred and heated to 70° C. Then 5.26 g (4 mL, 41.7 mmol) of dimethylsulfate was added via syringe over a period of 1 h. The temperature was increased to 90–95° C. and the mixture was stirred under nitrogen gas for a period of 18 h. Then DMF was distilled off under vacuum (0.1 mm, 35–40° C.) and the residue was taken into 30 mL of $CHCl_3$ and 30 mL of $H_2O$ mixture. The organic layer was separated, washed with 30 mL of conc. NaCl and dried over $Na_2SO_4$ (3 g). The solvent was evaporated under reduced pressure (14 mm) and the resulting brown oil (5.67 g) was purified by column chromatography (silicagel, $CHCl_3$/hexane (1:1)) to give 2.00 g (38%) of the product 36. For microanalysis crude 36 was recrystallized from hexane and dried under vacuum (0.1 mm, RT) for 2 days, mp 62–65° C. $^1$H NMR (300 MHz, $CDCl_3$): 6.64 (s, 1H, H6), 6.53 (s, 1H, H3), 4.68 (br. s, 1H, NH), 3.83 (s, 3H, H9), 3.79 (s, 3H, H10), 3.31 (m, 2H, H8), 2.78 (s, 6H, $N(CH_3)_2$), 2.74 (t, J=7.3 Hz, 2H, H7), 1.43 (s, 9H, $C(CH_3)$); $^{13}$C NMR (125.7 MHz, $CDCl_3$): 156.0, 151.6, 146.3, 141.5, 120.4, 114.3, 102.8, 78.8, 56.2, 56.0, 43.4, 41.1, 30.5, 28.6. EI-MS (70 eV, quadrupole), m/z (rel. intensity): 324 ($M^+$, 21), 251 (8), 194 (100), 149 (6). Anal. Calcd for $C_{17}H_{28}N_2O_4$: C, 62.92; H, 8.70; N, 8.63%. Found: C, 63.05; H, 8.93; N, 8.52%

E. Synthesis of Intermediate 37—(2,5-dimethoxy-4-dimethylaminophenethylamine)

A 10-mL round-bottomed flask equipped with a stirring was charged with 370 mg (1.14 mmol) of N-t-butoxycarbonyl-2,5-dimethoxy-4-dimethylaminophenethylamine (36), 1.0 mL of TFA and 0.3 mL of $H_2O$. The mixture was stirred at room temperature for 20 min. Most of TFA was removed by rotary evaporation (14 mm) at 25° C. and the resulting residue was dissolved in 1.5 mL of $H_2O$. The mixture was basified with sat. $K_2CO_3$ (5 mL) to pH 12 and extracted with $CHCl_3$ (3×7 mL). The extract was dried over $K_2CO_3$ (2 g), the solvent was evaporated to dryness and the resulting residue was dried under vacuum (0.1 mm) for a period of 24 h to give 250 mg (97%) of 37 as a light yellow oil. $^1$H NMR (300 MHz, $CDCl_3$): δ6.65 (s, 1H, H6), 6.53 (s, 1H, H3), 3.83 (s, 3H, H9), 3.78 (s, 3H, H10), 2.90 (t, J=6.9 Hz, 2H, H7), 2.77 (s, 6H, $N(CH_3)_2$), 2.69 (t, J=6.9 Hz, 2H, H8), 1.2 (br. s, 2H, $NH_2$); $^{13}$C NMR (75.5 MHz, $CDCl_3$): δ151.7, 146.2, 141.3, 121.2, 114.2, 103.1, 56.3, 56.0, 43,5 (=2C), 42.7, 34.5. EI-MS (70 eV, quadrupole), m/z (rel. intensity): 224 ($M^+$, 33), 194 (100), 164 (17), 149 (25).

E. Synthesis of Intermediate 38—(N-(2,5-Dimethoxy-4-dimethylaminophenethyl)-6,7-dihydro-8(5H)-quinolinone-2-carboxamide).

A 25-mL single-neck round-bottomed flask equipped with a stirring bar was charged with 0.29 g (1.52 mmol) of 6,7-dihydro-8(5H)-quinolinone-2-carboxylic acid (17), 0.19 g (1.90 mmol) of anhydrous triethylamine and 13 mL of $CH_2Cl_2$. The flask was closed with a septum with a needle connected to nitrogen gas line. The mixture was cooled to −20° C. and 1.82 mL of 1M solution of isopropylchloroformate in toluene (Aldrich) was added via syringe over a period of 1 h. The mixture was stirred below −10° C. for 0.5 h and 0.34 g (1.52 mmol) of 2,5-dimethoxy-4-dimethylaminophenethylamine (37) in 6 mL of $CH_2Cl_2$ was added via syringe over a period of 1 h. The stirring was continued for 1 h at −10° C., then the mixture was refrigerated for 12 h. The mixture was diluted with 10 mL of $CH_2Cl_2$, washed with sat. $NaHCO_3$ (3×20 mL), then with sat. NaCl (20 mL), then with $H_2O$ (20 mL) and dried over $MgSO_4$ (2 g). The solvent was evaporated under reduced pressure (14 mm) and the resulting brown viscous oil was dried under vacuum (0.1 mm) for 24 h to give 0.54 g (90%) of the product 38 as a viscous oil. $^1$H NMR (300 MHz, $CDCl_3$): δ8.38 (br., 1H, NH), 8.30 (d, J=7.6 Hz, 1H, H3), 7.81 (d, J=7.6 Hz, 1H, H4), 6.71 (s, 1H, H11), 6.55 (s, 1H, H12), 3.86 (s, 3H, H13), 3.81 (s, 3H, H14), 3.67 (m, 2H, H9), 3.09 (t, J=6.1 Hz, 2H, H10), 2.91 (t, J=7.3 Hz, 2H, H7), 2.83 (t, J=6.6 Hz, 2H, H5), 2.78 (s, 6H, $N(CH_3)_2$), 2.22 (m, 2H, H6); $^{13}$C NMR (75.5 MHz, $CDCl_3$): δ195.8, 163.8, 151.7, 149.7, 146.6, 146.3, 143.1, 141.6, 139.1, 125.4, 120.4, 114.2, 102.8, 56.3, 56.0, 43.4, 40.6, 40.0, 30.2, 29.5, 22.7. EI-MS (70 eV, quadrupole), m/z (rel. intensity): 397 ($M^+$, 14), 207 (33), 194 (100), 149 (7).

F. Synthesis of Intermediate 39K—(N-(2,5-Dimethoxy-4-dimethylaminophenethyl)-5,6,9,10-tetrahydro[1,10]phenanthrolino[2,3 -b][1,10] phenanthroline-13-carboxamide-2-carboxylic acid, potassium salt).

A 50-mL round-bottomed flask equipped with a stirring bar, condenser and nitrogen gas inlet was charged with 0.26 g (0.96 mmol) of 5,6-dihydro-9-amino-8-[1,10] phenanthrolinecarboxaldehyde-2-carboxylic acid (13), 12 mL of methanol and 20 mL of toluene. The mixture was heated to boiling and then KOH solution in methanol was added dropwise to achieve pH 9–10 (approximately 35 drops of 1.055 N KOH solution was required). Then 0.38 g (0.96 mmol) N-(2,5-dimethoxy-4-dimethylaminophenethyl)-6,7-dihydro-8(5H)-quinolinone-2-carboxamide (38) in 2 mL of methanol was added and the resulting mixture was heated under reflux, under nitrogen for 3.5 days. After the mixture was cooled to room temperature, 150 of ether was added and cooled in a freezer for a period of 3 h. The precipitate was collected by vacuum filtration, washed with 10 ML of ether and dried under vacuum (0.1 mm) to give 0.38 g of the first crop of potassium salt 39K. The mother liquor was evaporated and the resulting residue was brought into 5 mL of methanol. Then 70 mL of ether was added to cause precipitation. The precipitate was collected by vacuum filtration, washed with 10 mL of ether and dried under vacuum (0.1 mm) to give 0.14 g of the second crop of 39K. Both crops were combined to give 0.52 g (81%) of 39K. $^1$H NMR (300 MHz, DMSO-$d_6$): δ8.93 (t, J=5.9 Hz, 1H, NH), 8.31 (s, 1H, H7), 8.26 (s, 1H, H8), 8.07 (d, J=7.8 Hz, 1H, H3), 7.99 (d, J=7.8 Hz, 1H, H4), 7.97 (d, J=7.3 Hz, 1H, H12), 7.76 (d, J=7.8 Hz, 1H, H11), 6.75 (s, 1H, H17), 6.46 (s, 1H, H18), 3.74 (s, 3H, H19), 3.64 (s, 3H, H20), 3.52 (m, 2H, H15), 3.08–3.16 (br.m, 8H, H5,6,9,10), 2.83 (t, J=7.3 Hz, 2H, H16), 2.62 (s, 6H, $N(CH_3)_2$); $^{13}$C NMR (125.6 MHz, $D_2O$, ref. dioxane): δ171.4, 164.7, 153.8, 152.6, 152.4, 152.0, 151.1, 148.0, 147.7, 147.4, 146.5, 140.1, 138.4, 137.4, 134.8, 134.5, 133.0, 132.6, 125.1, 122.3, 122.0, 113.7, 104.3, 56.6, 55.9, 43.0, 38.9, 28.7, 25.9. IR (KBr): v3385(br.m), 2938(w), 2835(w), 2780(w), 1655(m), 1613(s), 1560(s), 1539(m), 1512(s), 1464(m), 1414(w), 1376(s), 1338(w), 1310(w), 1250(w), 1212(s), 1166(w), 1097(w), 1074(w), 1039(m), 933(w), 867(w), 806(w), 772(w), 738(w), 707(w), 625(w), 588(w). FAB-MS, m/z (rel. intensity): 707.4 (M+K, 22), 669.4 (M+1, 100), 625.5 (67), 609.4 (32), 595.4 (21). For microanalysis crude 39K was recrystallized from water and dried under vacuum (0.1 mm, RT) for 3 days, mp 315–320° C. with dec. Anal. calcd. for $C_{36}H_{33}KN_6O_5 2H_2O$: C, 61.33; H, 5.29; N, 11.92%. Found: C, 60.96; H, 5.48; N, 11.60%.

G. Synthesis of Intermediate 39H—(N-(2,5-Dimethoxy-4-dimethylaminophenethyl)-5,6,9,10-tetrahydro[1,10]phenanthrolino [2,3-b][1,10] phenanthroline-13-carboxamide-2-carboxylic acid).

A 25-mL Erlenmeyer flask equipped with a magnetic stirring bar was charged with 0.377 g (0.564 mmol) N-(2, 5-dimethoxy-4-dimethylaminophenethyl)-5,6,9,10-tetrahydro[1,10]phenanthrolino[2,3-b][1,10]phenanthroline-2-carboxamide-13-carboxylic acid, potassium salt (39K) and 10 mL of water. The mixture was ultrasonicated to aid faster formation of a clear solution. Then the solution was stirred and HCl was added dropwise to achieve pH 5.5–6.0 (about 3–4 drops of 15% HCl solution was required). The resulting suspension was refrigerated over a period of 24 h. The precipitate was collected by vacuum filtration, washed with water (2×3 mL) and dried under vacuum (0.1 mm, RT) over $P_2O_5$ for 24 h. to give 0.242 g (69%) of acid 39H, mp 202–204° C. with dec. $^1$H NMR (300 MHz, DMSO-$d_6$): δ8.77 (t, J=5.9 Hz, 1H, NH), 8.31 (s, 2H, H7,8), 8.06 (d, J=7.8 Hz, 1H, H3), 8.05 (d, J=7.3 Hz, 1H, H12), 7.98 (d, J=7.8 Hz, 1H, H4), 7.96 (d, J=7.8 Hz, 1H, H11), 6.75 (s, 1H, H17), 6.49 (s, 1H, H18), 3.82 (s, 3H, H19), 3.62 (s, 3H, H20), 3.52 (m, 2H, H15), 3.12–3.16 (br., 8H, H5,6,9,10), 2.82 (t, J=7.3 Hz, 2H, H16), 2.58 (s, 6H, N(CH$_3$)$_2$); $^{13}$C NMR (125.6 MHz, CDCl$_3$/CD$_4$OD (3.1)): δ171.1, 167.3, 165.0, 154.8, 154.4, 153.9, 151.6, 149.6, 149.4, 149.3, 146.1, 140.4, 139.3, 138.5, 138.0, 137.7, 135.6, 135.1, 133.9, 133.5, 125.3, 123.5, 123.1, 121.2, 114.0, 102.9, 55.9, 55.5, 43.2 (=2C), 39.8, 30.1, 27.5, 27.3, 27.0 (=2C). IR (KBr): ν3358(br. m), 2937(w), 2834(w), 2780(w), 1718(m), 1663(s), 1613(s), 1567(m), 1535(s), 1511(s), 1465(s), 1395(w), 1375(w), 1358(w), 1310(w), 1244(w), 1212(s), 1097(w), 1074(w), 1037(m), 927(w), 861(w), 811(w), 769(w), 738(w), 707(w), 670(w), 624(w), 585(w). FAB-MS, m/z (rel. intensity): 631.5 (M+1, 100), 587.5 (38), 571.4 (13). Anal. calcd. for $C_{36}H_{34}N_6O_5 \cdot H_2O$: C, 66.64; H, 5.60; N, 1296%. Found: C, 67.01; H, 5.33; N, 12.60%.

H. Synthesis of Compound IE—(5,6,9,10-Tetrahydro[1,10]phenanthrolino[2,3-b][1,10]phenanthroline-2-(N-(4-aminoethyl-N'-(4-tert-butoxycarbonyltoluidyl)naphthyridine))carboxamide-13-(N-(2,5-dimethoxy-4-dimethylaminophenethyl))carboxamide).

A 25-mL single-neck round-bottomed flask equipped with a stirring bar was charged with 166 mg (0.263 mmol) of N-(2,5-dimethoxy-4-dimethylaminophenethyl)-5,6,9,10-tetrahydro[1,10]phenanthrolino[2,3-b][1,10]phenanthroline-13-carboxamide-2-carboxylic acid (39H), 0.044 mL (39 mg, 0.315 mmol) of triethylamine and 8 mL of CH$_2$Cl$_2$. The flask was closed with a septum with a needle connected to nitrogen gas line. The mixture was cooled to −20° C. and a mixture of 0.268 mL of 1M solution of isopropylchloroformate in toluene (Aldrich) with 3 mL of CH$_2$Cl$_2$ was added via syringe over a period of 0.5 h. The mixture was stirred below −10° C. for 0.5 h and 117 mg (0.263 mmol) of N'-(4-tert-butoxycarbonyl-toluidyl)naphthyridine-4-aminoethylamine (40) in 4 mL of CH$_2$Cl$_2$ was added via syringe over a period of 0.5 h. The stirring was continued for 1 h at −10° C., then the mixture was refrigerated for 12 h. The mixture was diluted with 10 mL of CH$_2$Cl$_2$, washed with sat. NaHCO$_3$ (3×20 mL), then with sat. NaCl (20 mL), then with H$_2$O (20 mL) and dried over Na$_2$SO$_4$ (0.5 g). The solvent was evaporated under reduced pressure (14 mm) and the resulting residue (261 mg) was dissolved 3 mL of chloroform and passed through column (alumina, Fisher, 80–200 mesh) eluting with a CHCl$_3$/MeOH (99/1) mixture. Then the eluted solution was evaporated to dryness to give 244 mg of crude 11 (compound IE). The crude material was dissolved in 1 mL of CH$_2$Cl$_2$, then 50 mL of ethyl acetate was added which caused formation of cloudiness. The mixture was boiled for 5 min and the cloudiness was removed by filtration through Whatman #2 filter paper. Then the filtrate was concentrated by boiling out the solvent until the solution became cloudy (the volume of concentrated solution was about 20 mL). The hot mixture was let to cool to room temperature and after about 2 h the clear solution was carefully decanted from dark residue into a clean 50-mL round-bottomed flask. Then the clear solution was cooled in a freezer over a period of 12 h. The yellow precipitate was collected by vacuum filtration, washed with 2 mL of cold ethyl acetate and dried under vacuum (0.1 mm) for 24 h to give 130 mg (47%) of the first crop of final product 11 (compound IE). The filtrate from the first crop was concentrated to 4 mL by boiling out the solvent and cooled to room temperature. After 2 h., the clear solution was decanted from dark residue and cooled in a freezer over a period of 12 h. The yellow precipitate was collected by vacuum filtration, washed with 1 mL of cold ethyl acetate and dried under vacuum (0.1 mm) for 24 h to give 41 mg of the second crop of the final product 11. The combined crops gave 171 mg (61%) of pure product, mp 235–240° C. with dec. $^1$H NMR (300 MHz, DMSO-$d_6$): δ9.04 (t, J=5.4 Hz, 1H, NH22), 8.65 (d, J=8.8 Hz, 1H, H27), 8.58 (t, J=6.8 Hz, 1H, NH15), 8.38 (s, 2H, H7,8), 8.34 (d, J=7.3 Hz, 1H, H32), 8.17 (d, J=8.8 Hz, 1H, H30), 8.09 (m, 4H, H3,4,11,12), 8.00 (t, J=6.3 Hz, 1H, NH25), 7.81 (d, J=8.3 Hz, 2H, H35), 7.60 (dd, J1=7.3 Hz, J2=8.3 Hz, 1H, H31), 7.40 (d, J=8.3 Hz, 2H, H34), 6.92 (d, J=8.8 Hz, 1H, H26), 6.69 (s, 1H, H18), 6.32 (s, 1H, H19), 5.24 (s, 2H, H33), 3.74 (s, 3H, H20), 3.55 (s, 3H, H21), 3.2–3.5 (m, 14H, H5,6,9,10,16,23,24), 2.81 (br., 1H, NH17), 2.47 (s, 6H, N(CH$_3$)$_2$), 1.51 (s, 9H, C(CH$_3$)$_3$); $^{13}$C NMR (125.7 MHz, CDCl$_3$): δ166.5, 165.8, 164.8, 164.2, 164.0, 154.6, 154.1, 151.7, 150.5, 149.8, 149.6, 149.3, 146.3, 142.7, 141.6, 138.3, 137.8, 137.5, 135.0, 134.7, 134.5, 133.5, 133.3, 131.1, 131.0, 129.7, 128.8, 128.7, 128.1, 124.4, 123.4, 123.3, 123.2, 123.1, 122.1, 120.5, 114.0, 109.0, 103.4, 102.9, 81.0, 56.4, 56.1, 45.3, 43.4, 43.2, 39.9, 38.5, 30.0, 28.3, 27.6. IR (KBr): ν3367 (bm), 2935(w), 1685(m), 1648(s), 1616(w), 1581(s), 1559 (m), 1540(m), 1533(m), 1458(m), 1390(w), 1371(m), 1344 (m), 1311(w), 1294(m), 1245(w), 1212(m), 1184(w), 1141 (w), 1116(w), 1100(w), 1075(w), 1039(w), 991(w), 926(w) 858(w), 812(w), 772(m), 758(w), 708(w). FAB-MS, m/z (rel. intensity): 1058.7 (M+1, 100), 1002.6 (23). For microanalysis, a sample was dried under vacuum (0.1 mm) at 80° C. over a period of 7 days. Anal. calcd. for $C_{62}H_{59}N_9O_8 \cdot 2\ H_2O$: C, 68.05; H, 5.80; N, 11.52%. Found: C, 67.82; H, 5.48; N, 11.30%.

Example 6

Complexation Studies of Compound IA

UV-visible absorbance and fluorescence were examined. UV spectra were recorded on a Hewlett-Packard 8452A diode array UV-vis spectrophotometer, using a cell of 1 cm pathlength. Fluorescence spectra were recorded on a Photon Technology International QM-1 Steady state Fluorescence system. For UV-visible titrations stability constants ($K_s$) were calculated by fitting the data to the equation: $A_{obs}=(\epsilon_R[R]_t+[R]_t(\epsilon_{RG}-\epsilon_R)(K_s[G]_t+K_s[R]_t+1-\text{sqrt}((K_s[G]_t+K_s[R]_t+1)^2-4*[R]_t K_s^2[G]_t))/(2K_s[R]_t))$1 derived from $K_s=[G][R]/[RG]$, $[R]_t=[R]+[RG]$, $[G]_t=[G]+[RG]$, and $A_{obs}=(\epsilon_R[R]+\epsilon_{RG}[RG])$1. The experimentally determined parameters are as follows: $[R]_t$, the total concentration of a receptor; $[G]_t$, the total concentration of a guest; $A_{obs}$, the observed absorbance; $\epsilon_R$, the extinction coefficient of free receptor; 1, cell pathlength. The fitted parameters: $\epsilon_{RG}$, the extinction coefficient of a receptor complex with a guest, $K_s$, the stability constant. For fluorescense titrations stability constants ($K_s$) were calculated by fitting as the data to the equation: $I_{obs}=I_R+(I_{RG}-I_R)(K_s[G]_t+K_s[R]_t+1-\text{sqrt}((K_s[G]_t+K_s[R]_t+1)^2-4*[R]_tK_s^2[G]_t))/(2K_s[R]_t)$ derived from $K_s=[G][R]/[RG]$, $[R]_t=[R]+[RG]$, $[G]_t=[G]+[RG]$, and $I_{obs}=I_R+I_{RG}$. The experimentally determined parameters are as follows: $[R]_t$, the total concentration of a receptor; $[G]_t$, the total concentration of a guest; $I_{obs}$, the observed fluorescence intensity; $I_R$, the fluorescence intensity of free receptor at a given concentration. The fitted parameters: $I_{RG}$, the fluorescence intensity of a receptor complex with aguest at a given concentration, $K_s$, the stability constant. The calculations were performed using software Sigma Plot 1.02 (Jandel Scientific) with tolerance value 0.000100. The goodness of fit was evaluated by means of the Student's Paired t-Test (P-value>0.05).

Figure 6:
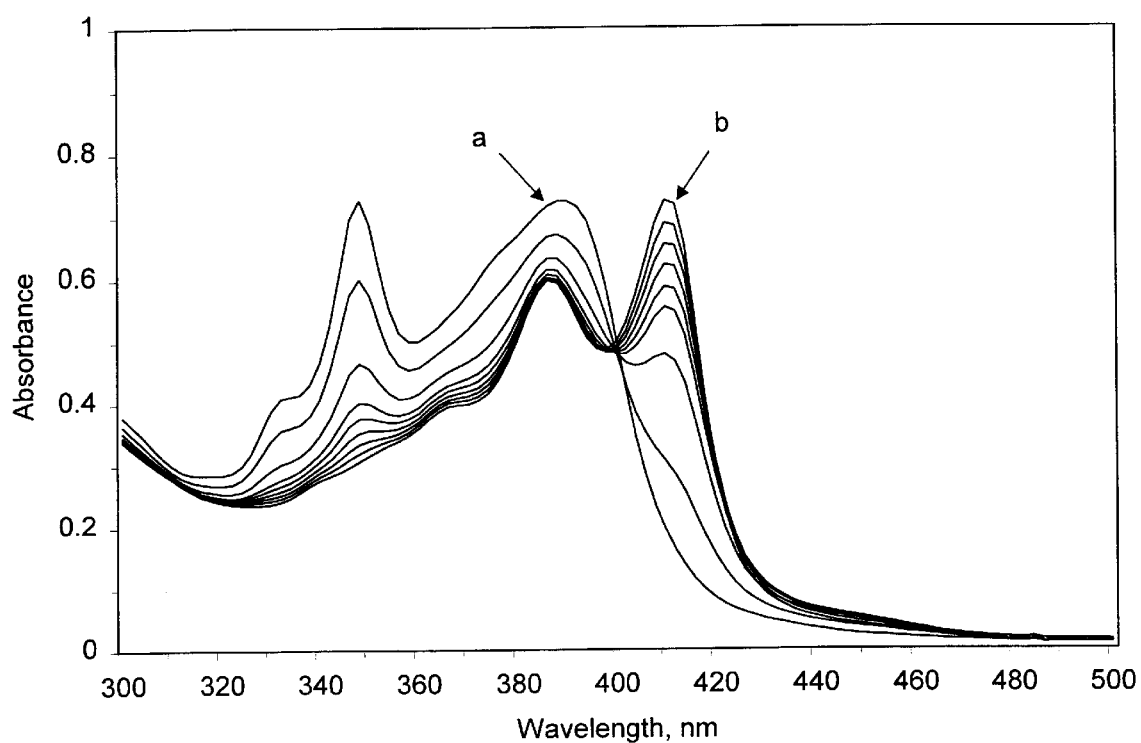
FIG. 6 is composite UV-Visible spectrum illustrating the change in absorbance for compound IA as a function of increasing N-methylguanidinium ion concentration: curve a—without N-methylguanidinium; and curve b—with 0.7 mM N-methylguanidinium.

UV-visible titrations was performed by first preparing a 30 µM receptor 5 (compound IA) stock solution in distilled water. A solution of N-methylguanidine hydrochloride in this stock receptor solution was added incrementally with a 25 µL pipette in eight (8) aliquots to the stock receptor solution used in the measurements to obtain a final 0.7 mM concentration of N-methylguanidine ion. The resulting composite spectra is shown in FIG. 6. As can been seen from FIG. 6, the complexation of the N-methylguanidinium ion guest with compound IA caused a planarization of the receptor molecule in which the naphthyridine group became more conjugated with the π-structure of the receptor base unit resulting in 25 nm bathochromic shift of the absorption band at 388 nm The following parameters were found from absorbance data measured at 410 nm: $\epsilon_R=6.50\times10^3$ cm$^{-1}$ M$^{-1}$, $\epsilon_{RG}=2.43\times10^4$ cm$^{-1}$ M$^{-1}$, $K_s=1.0\times10^5$ M$^{-1}$. The $K_s$ value for this complex correllates to a $K_d=0.01$ mM, which indicates that compound IA (5) binds N-methylguanidinium in water 430 times more strongly than the "arginine cork" (Bell et al., *Angew. Chem., Int. Ed. Engl.*, 1999, 38, 2543–2547).

Figure 7:
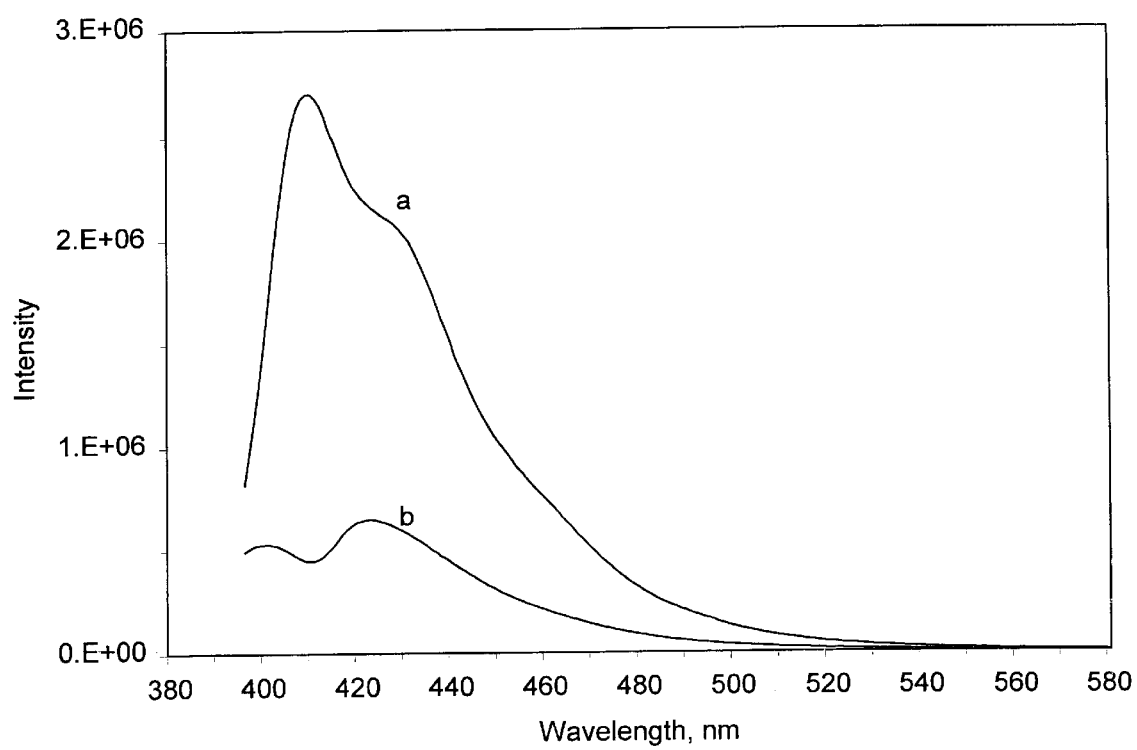
FIG. 7 is a composite emission spectrum illustrating the change in fluorescence intensity for 30 $\mu$M of compound IA excited at 388 nm: curve a—without N-methylguanidinium ion; and curve b—with 2 equivalents of N-methylguanidinium ion.

Fluorescence was performed using the 30 µM stock solution of the receptor (compound IA) in distilled water. An excitation wavelength of 388 nm was used to obtain the spectrum for the uncomplexed receptor. Thereafter, two (2) equivalents of N-methylmethylguanidinium hydrochloride were added and a spectrum was taken again. A composite spectrum is shown in FIG. 7, with curve (a) being the spectrum for the receptor prior to the addition of the guest and curve (b) being the spectrum after the addition of N-methylmethylguanidinium hydrochloride (i.e., guest). As can be seen from FIG. 7, complexation effectiviely quenches fluorescence with the maximum effective emission band at 410 nm being reduced to approximately 24% of its original intensity. This illustrates the strong binding to the N-methylmethylguanidinium ion by the receptor.

Example 7

Complexation Study of Compound IB

Figure 8:
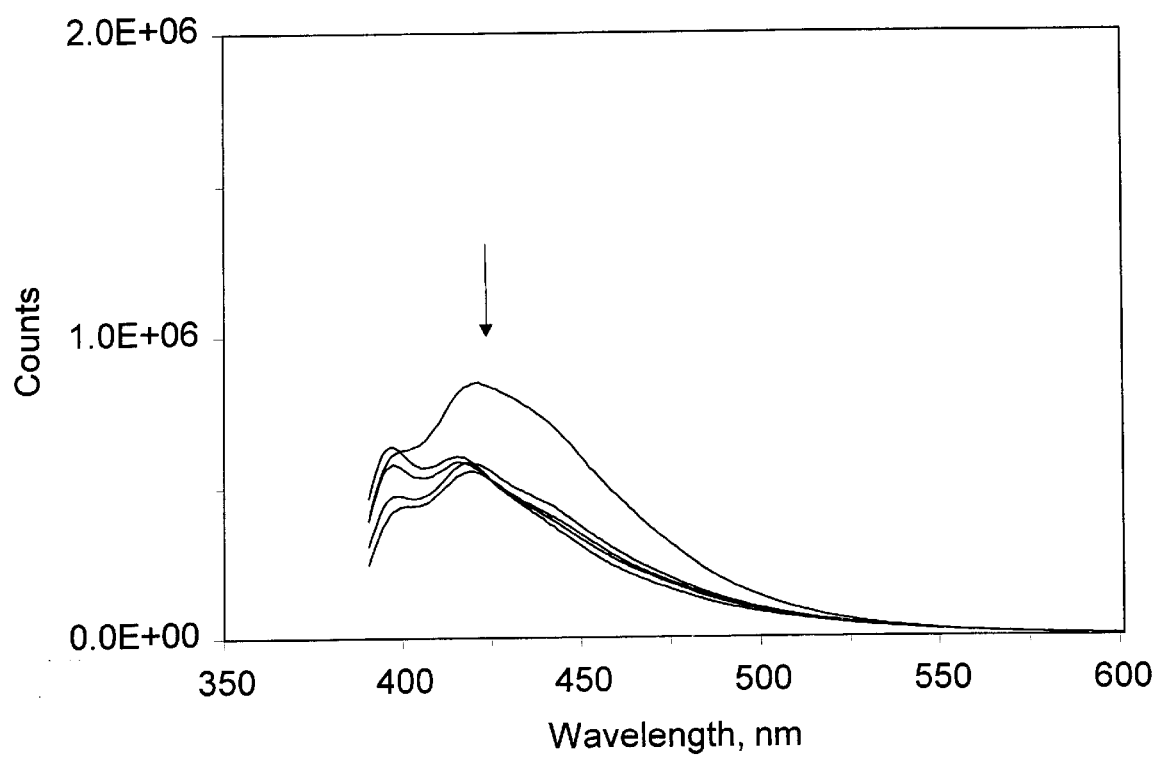
FIG. 8 is a composite emission spectrum illustrating the change in fluorescence intensity for compound IB excited at 384 nm as a function of increasing urea concentration

A fluorescence titration study was performed as follows: a stock solution of the receptor (compound IB) was prepared with distilled water. Using the equipment described in Example 6, an excitation wavelength of 384 nm was used to obtain the spectrum for the uncomplexed receptor. Thereafter, four (4) aliquots of a urea stock solution were added with fluorescence being measured after each addition. A composite spectrum is show in FIG. 8. As shown in FIG. 8, complexation resulted in fluorescence being quenched. The majority of the decrease in fluorescence occurred at a urea concentration below 17 mM indicating a $K_d$ with urea of less than 17 mM in water.

Example 8

Complexation Studies of Compound IC

Figure 9:
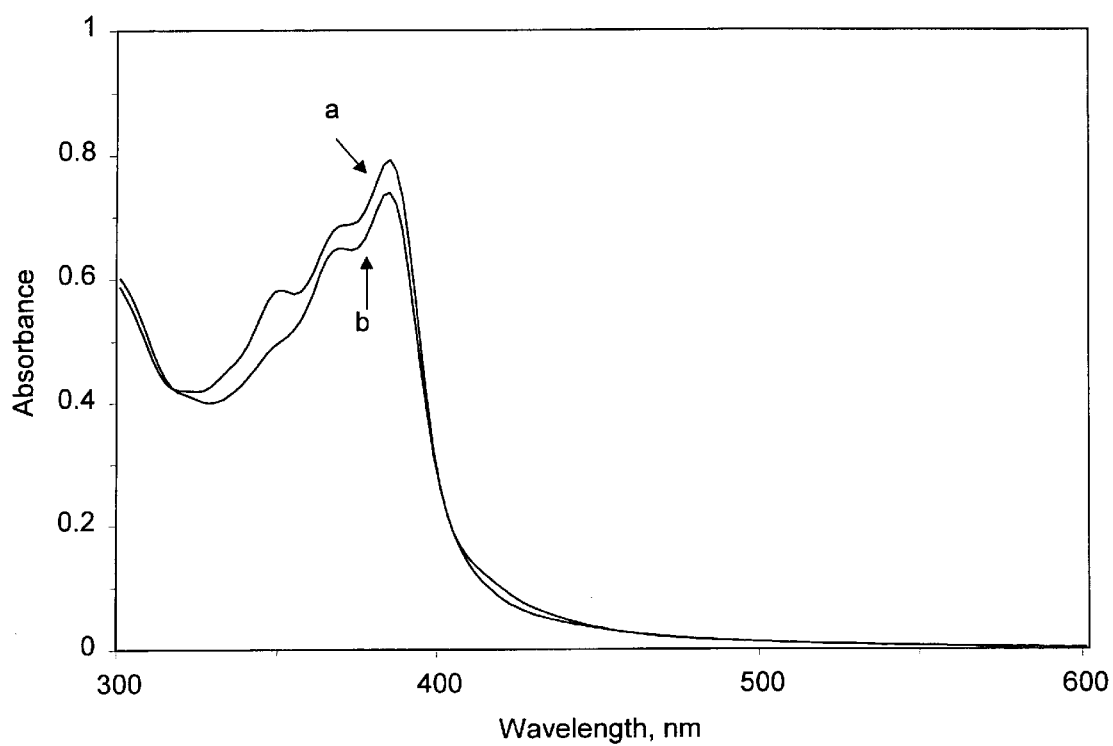
FIG. 9 is a composite absorption spectrum illustrating the change in fluorescence intensity for 30 $\mu$M of compound IC due to the addition of urea: curve a—without urea; and curve b—with 0.26 M urea.

A 30 µM stock DMSO solution of the receptor (compound IC) was prepared for measuring UV absorbance. Using the equipment of Example 6, absorbance for the uncomplexed recepted was measured. Thereafter, a 0.26 M urea solution in DMSO was added and absorbance measured again. A composite spectrum is shown in FIG. 9 with curve (a) representing the receptor (compound IC) without urea and curve (b) representing the complexexation of the receptor with urea.

Figure 10:
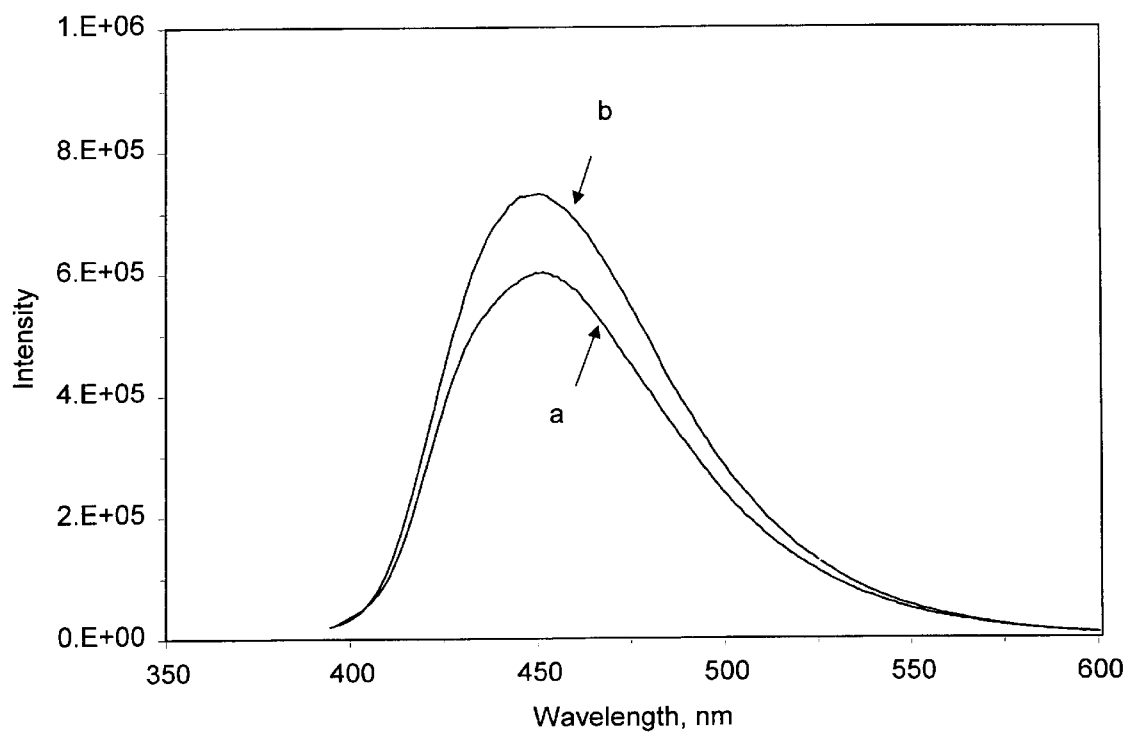
FIG. 10 is a composite emission spectrum illustrating the change in fluorescence intensity for 30 $\mu$M of compound IC excited at 384 nm: curve a—without urea; and curve b—with 0.26 M urea.

Fluorescence was measured for the stock receptor solution using an excitation wavelength of 384 nm with a peak emission being observed at 450 nm. The stock urea solution was then added and fluorescence was measured again. A composite spectrum is shown in FIG. 10, with curve (a) representing the receptor without urea and curve (b) representing the complexation of the receptor with urea. $K_d$ was estimated to be 33 mM for urea in DMSO.

Fluorescence was also measured using a 25 µM stock solution of the receptor in distilled water. An excitation wavelength of 392 nm was used where a peak emission was observed at 440 nm. The peak emission was observed to have twice the intensity of the peak emission observed in DMSO. A urea solution was prepared and added to the receptor solution to measure quenching due to complexation. $K_d$ was estimated to be 13 mM for urea in water.

Example 9

Complexation Study of Compound ID

Figure 11:
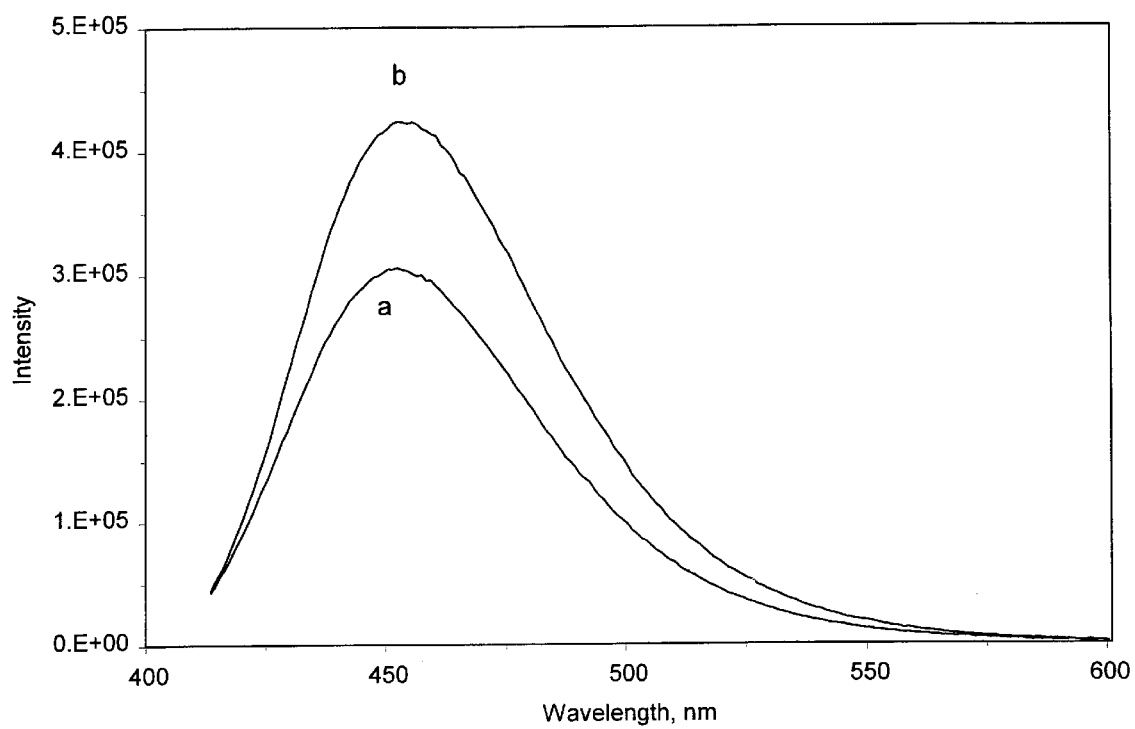
FIG. 11 is a composite emission spectrum illustrating the change in fluorescence intensity for 20 $\mu$M of compound ID excited at 407 nm: curve a—without urea; and curve b—with 0.17 M urea.

Fluorescence was measured for a 20 µM stock solution of compound ID in in a 98:2 (v/v) DMSO:water solvent system. An excitation wavelength of 407 nm was used with a peak emission being observed at 450 nm. A 0.17 M urea solution was then added and fluorescence measured again. A composite spectrum is shown in FIG. 11, with curve (a) representing the receptor (i.e., compound ID) without urea and curve (b) representing the complexation of the receptor with urea. $K_d$ was estimated to be 50 mM for urea in the DMSO: water solvent system.

Example 10

Complexation Study of Compound IE

Figure 12:
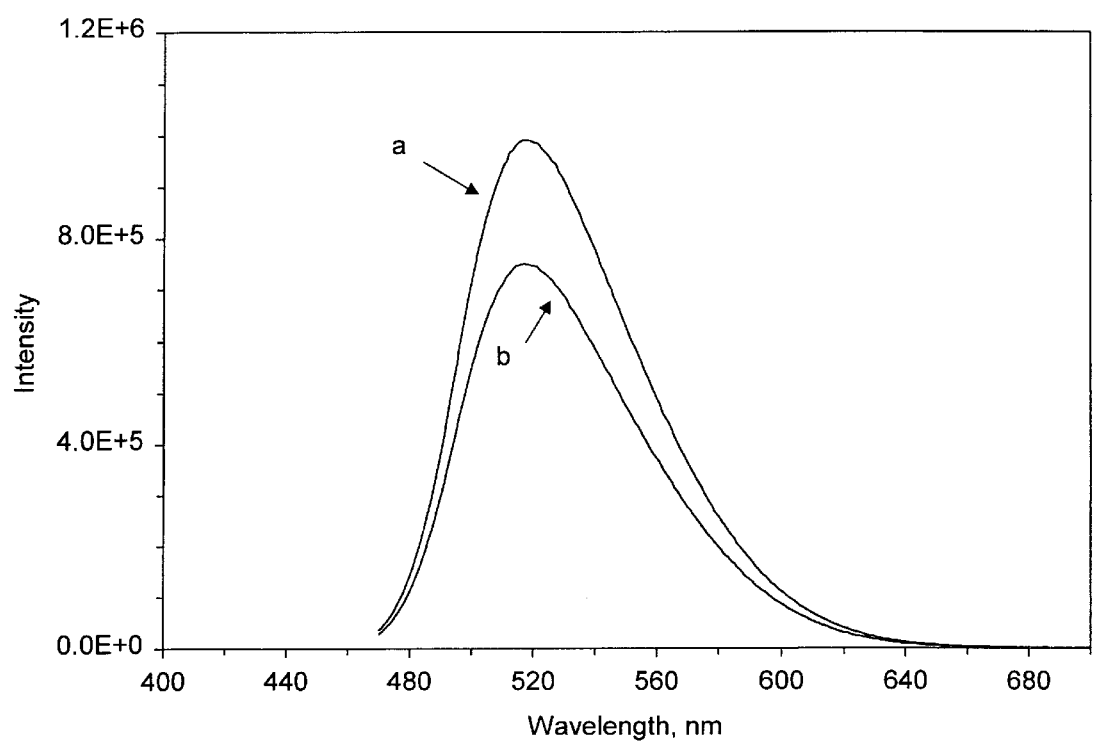
FIG. 12 is a composite emission spectrum illustrating the change in fluorescence intensity for 20 $\mu$M of compound ID excited at 460 nm: curve a—without urea; and curve b—with 20 equivalents of urea.

Fluorescence was measured for a 20 µM stock solution of compound IE in in a 1:1 (v/v) DMSO:CHCl$_3$ solvent system. An excitation wavelength of 460 nm was used with a peak emission being observed at 518 nm. Twenty equivalents of urea were then added and fluorescence measured again. A composite spectrum is shown in FIG. 12, with curve (a) representing the receptor (i.e., compound IE) without urea and curve (b) representing the complexation of the receptor with urea. $K_d$ was estimated to be 16 mM for urea in the DMSO:CHCl$_3$ solvent system.

We claim:
1. A multicyclic aromatic compound comprising the formula:

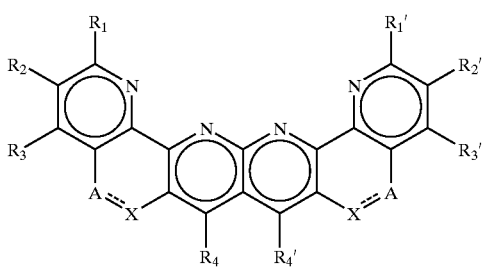

(I)

wherein $R_1$, $R_2$ and $R_3$ are the same or different and at least one is selected from the group consisting of a hydrophillic substituent, a directly or indirectly linked quencher molecule, a substituted or unsubstituted heterocyclic ring structure, and a combination thereof, with the remainder being hydrogen, wherein $R_1'$, $R_2'$ and $R_3'$ are the same or different and at least one is selected from the group consisting of a hydrophillic substituent, a substituted or unsubstituted heterocyclic ring structure, a directly or indirectly linked fluorophore, $R_1'$ and $R_2'$ together form a five- or six-membered cyclic ring fused to a substituted or unsubstituted heterocyclic ring structure, and a combination thereof, with the remainder being hydrogen;

wherein $R_4$ and $R_4'$ are the same or different and are selected from the group consisting of hydrogen, a hydrophillic substituent, a substituted or unsubstituted heterocyclic ring structure, a directly or indirectly linked quencher molecule, a directly or indirectly linked fluorophore and a combination thereof, or $R_4$ and $R_4'$ together form a five- or six-membered cyclic ring fused to a substituted or unsubstituted heterocyclic ring structure;

wherein A and A' are the same or different and are selected from the group consisting of carbon, nitrogen, oxygen, sulfur and a combination thereof;

wherein X and X' are the same and different and are a substituted or unsubstituted chain of 0 to 10 atoms selected from the group consisting of carbon, nitrogen, oxygen, sulfur, and a combination thereof;

wherein $R_1$ and $R_1'$ are not both selected from the group consisting of a carboxy group, a carboxylate and a combination thereof, when $R_2$, $R_2'$, $R_3$, $R_3'$, $R_4$, and $R_4'$ are hydrogen, A and A' are methylene, and X and X' are methylene; and wherein $R_1$ is not selected from the group consisting of a carboxy group and a carboxylate, when $R_1'$ is a substituted heterocyclic ring structure being a pyridine with substituents other than amines or alcohols.

2. The compound of claim 1, wherein the heterocyclic ring structure is selected from the group consisting of an unsubstituted pyridine, an substituted pyridine, an unsubstituted pyrimidine, a substituted pyrimidine, substituted naphthyridine, unsubstituted naphthyridine, and a combination thereof.

3. The compound of claim 1, wherein the hydrophillic substituent for $R_1'$, $R_2'$ and $R_3'$ is a hydrophillic substituent different from the at least one hydrophillic substituent for $R_1$, $R_2$ and $R_3$.

4. The compound of claim 1, wherein the hydrophillic substituent is selected from the group consisting of alcohols, amines, carboxylic acids, carboxylates, amides, sulfamides, sulfonic acids, sulfonates, sulfates, esters, thiol esters, ethers, thiols, thiolates, thiolethers, and combinations thereof.

5. The compound of claim 1, wherein $R_1$, $R_2$, $R_3$, or $R_4$ is a quencher molecule and $R_1'$, $R_2'$, $R_3'$, or $R_4'$ is a fluorophore.

6. The compound of claim 1, wherein $R_1$ is selected from the group consisting of a carboxylic acid and a carboxylate, and wherein $R_1'$ and $R_2'$ form a six-membered cyclic ring fused to a substituted or unsubstituted naphthyridine.

7. The compound of claim 6, wherein the compound has the formula:

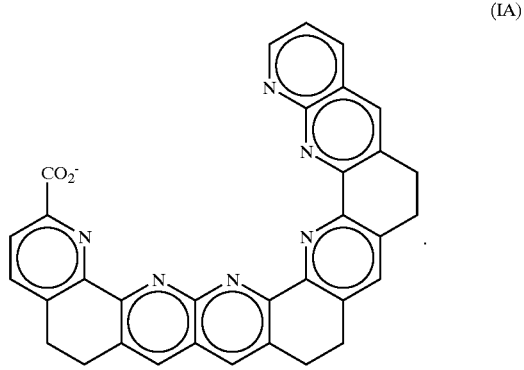

(IA)

8. The compound of claim 6, wherein the compound has the formula:

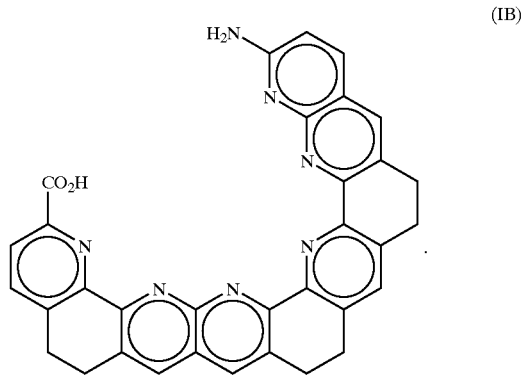

(IB)

9. The compound of claim 1, wherein $R_1$ is selected from the group consisting of a carboxylic acid and a carboxylate, and wherein $R_1'$ is selected from the group consisting of a substituted pyridine and an unsubstituted pyridine.

10. The compound of claim 9, wherein the compound has the formula:

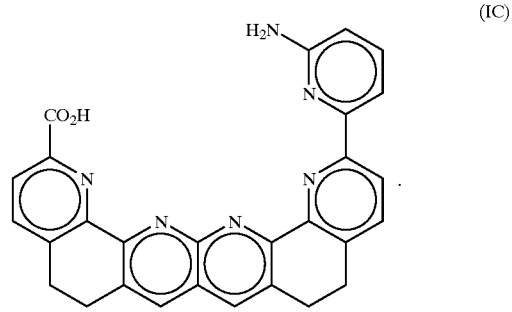

(IC)

11. The compound of claim 1, wherein $R_1$ is selected from the group consisting of a carboxylic acid and a carboxylate, $R_1'$ is selected from the group consisting of a substituted pyrimidine and an unsubstituted pyrimidine.

12. The compound of claim 11, wherein the compound has the formula:

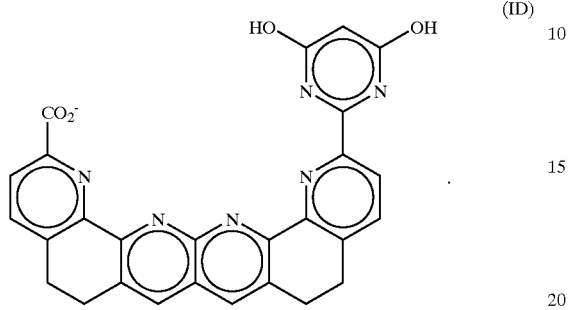

(ID)

13. The compound of claim 5, wherein $R_1$ is a indirectly linked quencher molecule and $R_1'$ is an indirectly linked fluorophore.

14. The compound of claim 13, wherein the quencher molecule linked to an amide via a n-terminus, and the flourophore linked to an amide via a n-terminus.

15. The compound of claim 5, wherein the quencher molecule is 4-dimethylamino-2,5-dimethoxyphenyl, and the fluorophore is a substituted 4-amino-1,8-naphthalimidyl.

16. The compound of claim 14, wherein the compound has the formula:

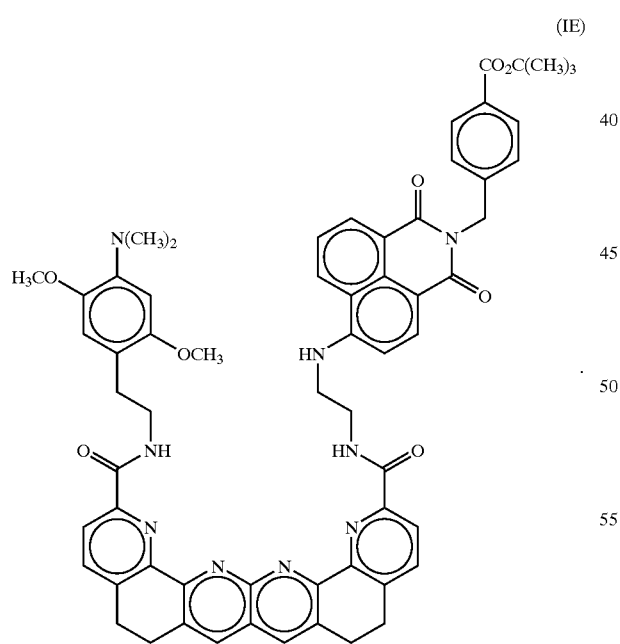

(IE)

17. A method of forming a complex with urea, guanidine, mono- or di-substituted alkyl guanidines, derivatives thereof and acid addition salts thereof, which comprises:

(a) providing a multicylic aromatic compound having the formula:

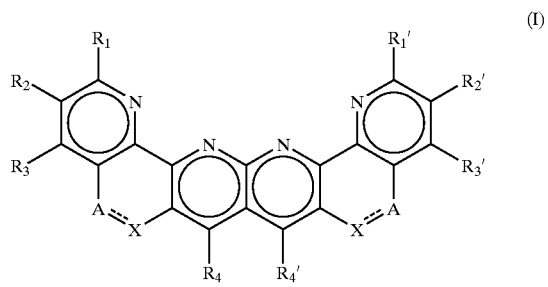

(I)

wherein $R_1$, $R_2$ and $R_3$ are the same or different and at least one is selected from the group consisting of a hydrophillic substituent, a directly or indirectly linked quencher molecule, a substituted or unsubstituted heterocyclic ring structure, and a combination thereof, with the remainder being hydrogen, wherein $R_1'$, $R_2'$ and $R_3'$ are the same or different and at least one is selected from the group consisting of a hydrophillic substituent, a substituted or unsubstituted heterocyclic ring structure, a directly or indirectly linked fluorophore, $R_1'$ and $R_2'$ together form a five- or six-membered cyclic ring fused to a substituted or unsubstituted heterocyclic ring structure, and a combination thereof, with the remainder being hydrogen;

wherein $R_4$ and $R_4'$ are the same or different and are selected from the group consisting of hydrogen, a hydrophillic substituent, a substituted or unsubstituted heterocyclic ring structure, a directly or indirectly linked quencher molecule, a directly or indirectly linked fluorophore and a combination thereof, or $R_4$ and $R_4'$ together form a five- or six-membered cyclic ring fused to a substituted or unsubstituted heterocyclic ring structure;

wherein A and A' are the same or different and are selected from the group consisting of carbon, nitrogen, oxygen and sulfur;

wherein X and X' are the same and different and are a substituted or unsubstituted chain of 0 to 10 atoms selected from the group consisting of carbon, nitrogen, oxygen, sulfur, and a combination thereof;

wherein $R_1$ and $R_1'$ are not both selected from the group consisting of a carboxy group, a carboxylate and a combination thereof, when $R_2$, $R_2'$, $R_3$, $R_3'$, $R_4$, and $R_4'$ are hydrogen, A and A' are methylene, and X and X' are methylene; and wherein $R_1$ is not selected from the group consisting of a carboxy group and a carboxylate, when $R_1'$ is a substituted heterocyclic ring structure being a pyridine with at least one substituent other than an amine or alcohol; and (b) contacting the multicylic aromatic compound with a sample including at least one component selected from the group consisting of urea, guanidine, mono- or di-substituted alkyl guanidines, derivatives thereof and acid addition salts thereof.

18. The method of claim 17, further comprising measuring a change in optical signalling for the multicylic aromatic compound due to complex formation.

19. The method of claim 18, further comprising correlating the change in optical signalling to a concentration of the component in the sample.

20. The method of claim 19, wherein the change in optical signalling is a change in luminescene.

21. The method of claim 20, wherein the luminescence is fluorescensce.

* * * * *